(12) United States Patent
Menges et al.

(10) Patent No.: US 6,383,986 B1
(45) Date of Patent: May 7, 2002

(54) SUBSTITUTED 2-(BENZOARYL)PYRIDINES

(75) Inventors: Markus Menges, Bensheim; Gerhard Hamprecht, Weinheim; Olaf Menke, Altleiningen; Robert Reinhard, Ludwigshafen; Peter Schäfer, Ottersheim; Cyrill Zagar, Ludwigshafen; Karl-Otto Westphalen, Speyer; Martina Otten, Ludwigshafen; Helmut Walter, Obrigheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/462,583
(22) PCT Filed: Jun. 23, 1998
(86) PCT No.: PCT/EP98/03833
§ 371 Date: Jan. 11, 2000
§ 102(e) Date: Jan. 11, 2000
(87) PCT Pub. No.: WO99/06394
PCT Pub. Date: Feb. 11, 1999

(30) Foreign Application Priority Data

Jul. 14, 1997 (DE) .......................................... 197 30 078

(51) Int. Cl.[7] .................. A01N 43/40; A01N 43/10; C07D 413/10; C07D 417/04; C07D 419/02
(52) U.S. Cl. .................. 504/251; 504/244; 504/252; 504/253; 546/270.1; 546/271.7
(58) Field of Search ................. 504/244, 254, 504/255, 251, 260, 252; 546/268.1, 268.4, 269.1, 268.7, 270.1, 271.7

(56) References Cited

U.S. PATENT DOCUMENTS

| | | | | |
|---|---|---|---|---|
| 4,891,428 A | | 1/1990 | Nordhoff et al. ............ | 546/278 |
| 5,733,850 A | * | 3/1998 | Schafer et al. ............. | 504/244 |
| 6,010,980 A | * | 1/2000 | Schafer et al. ............. | 504/244 |

FOREIGN PATENT DOCUMENTS

| | | |
|---|---|---|
| DE | 3605343 A1 | 8/1987 |
| DE | 19633751 * | 8/1996 |
| EP | 0270760 A1 | 6/1988 |
| EP | 0616807 A1 | 9/1994 |
| GB | 2174395 A | 11/1986 |
| WO | WO96/11917 | 4/1996 |
| WO | WO98/27090 | 6/1998 |

OTHER PUBLICATIONS

Shigyo et al. "Synthesis and Antiarrhythmic Activity of Disubstituted Phenylpyridine Derivative" Chem. Pharm. Bull. 41(9) pp. 1573–1582.

Abromovitch et al. "9882k Pyrido,2–b indazole and its derivatives" Chemical Abstracts, vol. 83, No. 1 Jul. 7, 1975, p. 825.

Abromovitch et al. "A new route to pyrido[1,2–b]indazole and its derivatives is described and the nitration of the parent compound is reported. The formation of β–carbolines as byproducts is discussed." Journ. Heterocycl. Chem., vol. 11(6) Dec. 1974, pp. 857–861.

Abromovitch et al. "Reaction of Pyridine i–Oxides and N–Iminopyridinium Ylides with Diazonium Salts. N–Arylosy pyridinium Salts and Their Base–Catalyzed Rearrangement" J. Org. Chem., vol. 41, No. 10, 1976 pp. 1717–1724.

\* cited by examiner

*Primary Examiner*—Alan L. Rotman
*Assistant Examiner*—Rita Desai
(74) *Attorney, Agent, or Firm*—Keil & Weinkauf

(57) ABSTRACT

2-(Benzaryl)pyridines I

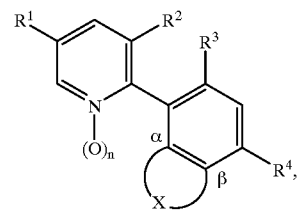

and salts thereof where n=zero, 1;

$R^1$=H, CN, $NO_2$, $NH_2$, OH, SH, $SO_2$—OH, $SO_2$—Cl, $SO_2$—$NH_2$, halogen, optionally halogenated alkyl, alkoxy, alkylthio, alkylsulfinyl, alkylsulfonyl, alkylaminosulfonyl, dialkylaminosulfonyl;

$R^2$, $R^3$=H, halogen;

$R^4$=CN, OH, halogen, alkoxy or optionally substituted benzyloxy;

X=—Y—C($ZR^5$)=N— where the nitrogen is attached to α or β and Y=—O—, —S—, —N($R^6$)—;

Z=a chemical bond, —O—, —S—, —S(O)—, —$SO_2$—, —N($R^7$)—;

$R^5$, $R^6$, $R^7$=H, optionally substituted alkyl, alkenyl, alkynyl, cycloalkyl, phenyl or 3- to 7-membered heterocyclyl; or $R^5$=H, CN, SH, $NH_2$, halogen, —$CH_2$—CH(halogen)-$R^8$, —CH=CH—$R^8$ or —CH=C(halogen)-$R^8$ ($R^8$= COOH, alkoxycarbonyl, alkylthiocarbonyl, $CONH_2$, alkylaminocarbonyl or dialkylaminocarbonyl), when Z=a chemical bond; or $R^5$+$R^7$=1,3-propylene, tetramethylene, pentamethylene or ethyleneoxyethylene.

Use: as herbicides, desiccants or defoliants.

14 Claims, No Drawings

SUBSTITUTED 2-(BENZOARYL)PYRIDINES

The present invention relates to novel substituted 2-(benzaryl)pyridines of the formula I

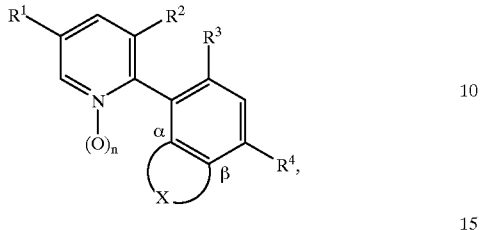

where:

n is zero or 1;

$R^1$ is hydrogen, cyano, nitro, amino, hydroxyl, mercapto, hydroxysulfonyl, chlorosulfonyl, aminosulfonyl, halogen, $C_1-C_6$-alkyl, $C_1-C_6$-haloalkyl, $C_1-C_6$-alkoxy, $C_1-C_6$-haloalkoxy, $C_1-C_6$-alkylthio, $C_1-C_6$-haloalkylthio, $C_1-C_6$-alkylsulfinyl, $C_1-C_6$-haloalkylsulfinyl, $C_1-C_6$-alkylsulfonyl, $C_1-C_6$-haloalkylsulfonyl, $C_1-C_6$-alkylaminosulfonyl or di($C_1-C_6$-alkyl)aminosulfonyl;

$R^2$ and $R^3$ independently of one another are each hydrogen or halogen;

$R^4$ is cyano, hydroxyl, halogen, $C_1-C_6$-alkoxy or benzyloxy, where the phenyl ring may be unsubstituted or may carry one to three substituents, in each case selected from the group consisting of hydroxyl, halogen, $C_1-C_6$-alkyl, $C_1-C_6$-haloalkyl, $C_1-C_6$-alkoxy, $C_1-C_6$-haloalkoxy, hydroxycarbonyl, ($C_1-C_6$-alkoxy)carbonyl and ($C_1-C_6$-alkoxy)carbonyl-$C_1-C_6$-alkoxy;

X is the —Y—C($ZR^5$)=N— moiety of a hetaryl ring, where the nitrogen may be attached to α or β and Y is oxygen, sulfur or —N($R^6$)—;

Z is a chemical bond, oxygen, sulfur, —S(O)—, —SO$_2$— or —N($R^7$)—;

$R^5$, $R^6$ and $R^7$ independently of one another are each hydrogen, $C_1-C_6$-alkyl, $C_1-C_6$-haloalkyl, cyano-$C_1-C_4$-alkyl, hydroxy-$C_1-C_4$-alkyl, $C_3-C_6$-alkenyl, cyano-$C_3-C_6$-alkenyl, $C_3-C_6$-haloalkenyl, $C_3-C_6$-alkynyl, cyano-$C_3-C_6$-alkynyl, $C_3-C_6$-haloalkynyl, $C_1-C_4$-alkoxy-$C_1-C_4$-alkyl, $C_1-C_4$-haloalkoxy-$C_1-C_4$-alkyl, $C_3-C_4$-alkenyloxy-$C_1-C_4$-alkyl, $C_3-C_4$-alkynyloxy-$C_1-C_4$-alkyl, $C_3-C_8$-cycloalkyloxy-$C_1-C_4$-alkyl, amino-$C_1-C_4$-alkyl, $C_1-C_4$-alkylamino-$C_1-C_4$-alkyl, di($C_1-C_4$-alkyl)amino-$C_1-C_4$-alkyl, $C_1-C_4$-alkylthio-$C_1-C_4$-alkyl, $C_1-C_4$-haloalkylthio-$C_1-C_4$-alkyl, $C_3-C_4$-alkenylthio-$C_1-C_4$-alkyl, $C_3-C_4$-alkynylthio-$C_1-C_4$-alkyl, $C_1-C_4$-alkylsulfinyl-$C_1-C_4$-alkyl, $C_1-C_4$-haloalkylsulfinyl-$C_1-C_4$-alkyl, $C_3-C_4$-alkenylsulfinyl-$C_1-C_4$-alkyl, $C_3-C_4$-alkynylsulfinyl-$C_1-C_4$-alkyl, $C_1-C_4$-alkylsulfonyl-$C_1-C_4$-alkyl, $C_1-C_4$-haloalkylsulfonyl-$C_1-C_4$-alkyl, $C_3-C_4$-alkenylsulfonyl-$C_1-C_4$-alkyl, $C_3-C_4$-alkynylsulfonyl-$C_1-C_4$-alkyl, ($C_1-C_4$-alkoxy)carbonyl, hydroxycarbonyl-$C_1-C_4$-alkyl, ($C_1-C_4$-alkoxy)carbonyl-$C_1-C_4$-alkyl, ($C_1-C_4$-alkylthio)carbonyl-$C_1-C_4$-alkyl, aminocarbonyl-$C_1-C_4$-alkyl, $C_1-C_4$-alkylaminocarbonyl-$C_1-C_4$-alkyl, di($C_1-C_4$-alkyl)aminocarbonyl-$C_1-C_4$-alkyl, $C_3-C_8$-cycloalkyl, $C_3-C_8$-cycloalkyl-$C_1-C_4$-alkyl, phenyl, phenyl-$C_1-C_4$-alkyl, 3- to 7-membered heterocyclyl or heterocyclyl-$C_1-C_4$-alkyl, where each cycloalkyl and each heterocyclyl ring may contain a carbonyl or thiocarbonyl ring member, and where each cycloalkyl, phenyl and heterocyclyl ring may be unsubstituted or may carry one to four substituents, in each case selected from the group consisting of cyano, nitro, amino, hydroxyl, carboxy, halogen, $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-haloalkylthio, $C_1-C_4$-alkylsulfonyl, $C_1-C_4$-haloalkylsulfonyl, ($C_1-C_4$-alkoxy)carbonyl, ($C_1-C_4$-alkyl)carbonyl, ($C_1-C_4$-haloalkyl)carbonyl, ($C_1-C_4$-alkyl)carbonyloxy, ($C_1-C_4$-haloalkyl)carbonyloxy and di($C_1-C_4$-alkyl)amino, or, if Z is a chemical bond, $R^5$ is also hydrogen, cyano, mercapto, amino, halogen, —CH$_2$—CH(halogen)-$R^8$, —CH=CH—$R^8$ or —CH=C(halogen)-$R^8$, where $R^8$ is hydroxycarbonyl, ($C_1-C_4$-alkoxy)carbonyl, ($C_1-C_4$-alkylthio)carbonyl, aminocarbonyl, $C_1-C_4$-alkylaminocarbonyl or di($C_1-C_4$-alkyl)aminocarbonyl, or $R^5$ and $R^7$ together are a 1,3-propylene, tetramethylene, pentamethylene or ethyleneoxyethylene chain which may in each case be unsubstituted or may carry one to four $C_1-C_4$-alkyl groups or one or two ($C_1-C_4$-alkoxy)carbonyl groups, and the agriculturally useful salts of these compounds I.

The invention further relates to the use of the compounds I as herbicides and/or the desiccation/defoliation of plants, herbicides and compositions for the desiccation and/or defoliation of plants which comprise the compounds I as active substances, processes for preparing the compounds I and herbicides and compositions for the desiccation/defoliation of plants using the compounds I, Methods for controlling undesirable vegetation and for the desiccation/defoliation of plants using the compounds I, and novel intermediates of the formulae Va/Vb, VIa/VIb and VIIIa/VIIIb, from which the compounds I are obtainable.

WO 96/11917 describes certain benzoxazoles and benzthiazoles and EP-A 616 807 describes certain benzimidazoles having various pharmaceutical activities whose general formulae—if the substituents are chosen appropriately—formally also include some of the present compounds I.

It is an object of the present invention to provide novel herbicidal 2-arylpyridines which allow better selective control of undesirable plants than known compounds. It is a further object to provide novel compounds which have a desiccant/defoliant action.

We have found that this object is achieved by the present substituted 2-(benzaryl)pyridines of the formula I.

Furthermore, we have found herbicides which comprise the compounds I and have a very good herbicidal activity. Moreover, we have found processes for preparing these compositions and methods for controlling undesirable vegetation using the compounds I.

Furthermore, we have found that the compounds I are also suitable for the desiccation/defoliation of parts of plants, suitable plants being crop plants such as cotton, potatoes, oilseed rape, sunflower, soybean or field beans, in particular cotton. In this regard, we have found compositions for the desiccation and/or defoliation of plants, processes for preparing these compositions and methods for the desiccation and/or defoliation of plants using the compounds I.

Depending on the substitution pattern, the compounds of the formula I can contain one or more chiral centers, in which case they exist in the form of enantiomer or diastereomer mixtures. E/Z isomers may also be possible for compounds I having at least one olefinic radical. The invention relates to the pure enantiomers or diastereomers and also to mixtures thereof.

The organic moieties mentioned in the definition of the substituents $R^1$, $R^4$ to $R^8$ or as radicals on cycloalkyl, phenyl or heterocyclic rings or on the chain $R^5$–$R^7$ are—like the term halogen—collective terms for individual listings of the individual group members. All carbon chains, i.e. all the alkyl, haloalkyl, cyanoalkyl, hydroxyalkyl, aminoalkyl, hydroxycarbonylalkyl, aminocarbonylalkyl, cycloalkylalkyl, phenylalkyl, heterocyclylalkyl, alkenyl, haloalkenyl, cyanoalkenyl, alkynyl, haloalkynyl and cyanoalkynyl moieties, can be straight-chain or branched. Halogenated substituents preferably carry one to five identical or different halogens. The term halogen represents in each case fluorine, chlorine, bromine or iodine.

Other examples of meanings are:

$C_1$–$C_4$-alkyl: $CH_3$, $C_2H_5$, n-propyl, 1-methylethyl, n-butyl, 1-methylpropyl, 2-methylpropyl and $C(CH_3)_3$;

$C_1$–$C_4$-haloalkyl: a $C_1$–$C_4$-alkyl radical as mentioned above which is partially or fully substituted by fluorine, chlorine, bromine and/or iodine, ie. for example $CH_2Cl$, dichloromethyl, trichloromethyl, $CH_2F$, $CHF_2$, $CF_3$, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, $C_2F_5$, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, 1-fluoromethyl-2-fluoroethyl, 1-chloromethyl-2-chloroethyl, 1-bromomethyl-2-bromoethyl, 4-fluorobutyl, 4-chlorobutyl, 4-bromobutyl or n-$C_4F_9$;

$C_1$–$C_6$-alkyl: $C_1$–$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably $CH_3$, $C_2H_5$, $CH_2$—$C_2H_5$, $CH(CH_3)_2$, n-butyl, $C(CH_3)_3$, n-pentyl or n-hexyl;

$C_1$–$C_6$-haloalkyl: a $C_1$–$C_6$-alkyl radical as mentioned above which is partially or fully substituted by fluorine, chlorine, bromine and/or iodine, ie. for example one of the radicals mentioned under $C_1$–$C_4$-haloalkyl, and also 5-fluoro-1-pentyl, 5-chloro-1-pentyl, 5-bromo-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl;

cyano-$C_1$–$C_4$-alkyl: $CH_2CN$, 1-cyanoethyl, 2-cyanoethyl, 1-cyanoprop-1-yl, 2-cyanoprop-1-yl, 3-cyanoprop-1-yl, 1-cyanobut-1-yl, 2-cyanobut-1-yl, 3-cyanobut-1-yl, 4-cyanobut-1-yl, 1-cyanobut-2-yl, 2-cyanobut-2-yl, 3-cyanobut-2-yl, 4-cyanobut-2-yl, 1-($CH_2CN$)eth-1-yl, 1-($CH_2CN$)-1-($CH_3$)eth-1-yl or 1-($CH_2CN$)prop-1-yl;

hydroxy-$C_1$–$C_4$-alkyl: $CH_2OH$, 1-hydroxyethyl, 2-hydroxyethyl, 1-hydroxyprop-1-yl, 2-hydroxyprop-1-yl, 3-hydroxyprop-1-yl, 1-hydroxybut-1-yl, 2-hydroxybut-1-yl, 3-hydroxybut-1-yl, 4-hydroxybut-1-yl, 1-hydroxybut-2-yl, 2-hydroxybut-2-yl, 3-hydroxybut-2-yl, 4-hydroxybut-2-yl, 1-($CH_2OH$)eth-1-yl, 1-($CH_2OH$)-1-($CH_3$)eth-1-yl or 1-($CH_2OH$)prop-1-yl;

amino-$C_1$–$C_4$-alkyl: $CH_2NH_2$, 1-aminoethyl, 2-aminoethyl, 1-aminoprop-1-yl, 2-aminoprop-1-yl, 3-aminoprop-1-yl, 1-aminobut-1-yl, 2-aminobut-1-yl, 3-aminobut-1-yl, 4-aminobut-1-yl, 1-aminobut-2-yl, 2-aminobut-2-yl, 3-aminobut-2-yl, 4-aminobut-2-yl, 1-($CH_2NH_2$)eth-1-yl, 1-($CH_2NH_2$)-1-($CH_3$)eth-1-yl or 1-($CH_2NH_2$)prop-1-yl;

hydroxycarbonyl-$C_1$–$C_4$-alkyl: $CH_2COOH$, 1-(COOH)ethyl, 2-(COOH)ethyl, 1-(COOH)prop-1-yl, 2-(COOH)prop-1-yl, 3-(COOH)-prop-1-yl, 1-(COOH)but-1-yl, 2-(COOH)but-1-yl, 3-(COOH)but-1-yl, 4-(COOH)but-1-yl, 1-(COOH)but-2-yl, 2-(COOH)but-2-yl, 3-(COOH)but-2-yl, 4-(COOH)but-2-yl, 1-($CH_2COOH$)eth-1-yl, 1-($CH_2COOH$)-1-($CH_3$)eth-1-yl or 1-($CH_2COOH$)prop-1-yl;

aminocarbonyl-$C_1$–$C_4$-alkyl: $CH_2CONH_2$, 1-($CONH_2$)ethyl, 2-($CONH_2$)ethyl, 1-($CONH_2$)prop-1-yl, 2-($CONH_2$)prop-1-yl, 3-($CONH_2$)prop-1-yl, 1-($CONH_2$)but-1-yl, 2-($CONH_2$)but-1-yl, 3-($CONH_2$)but-1-yl, 4-($CONH_2$)but-1-yl, 1-($CONH_2$)but-2-yl, 2-($CONH_2$)but-2-yl, 3-($CONH_2$)but-2-yl, 4-($CONH_2$)but-2-yl, 1-($CH_2CONH_2$)eth-1-yl, 1-($CH_2CONH_2$)-1-($CH_3$)eth-1-yl or 1-($CH_2CONH_2$)prop-1-yl;

phenyl-$C_1$–$C_4$-alkyl: benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-phenylmethyleth-1-yl, 1-phenylmethyl-1-methyleth-1-yl or 1-phenylmethylprop-1-yl, preferably benzyl or 2-phenylethyl;

heterocyclyl-$C_1$–$C_4$-alkyl: heterocyclylmethyl, 1-heterocyclylethyl, 2-heterocyclylethyl, 1-heterocyclylprop-1-yl, 2-heterocyclylprop-1-yl, 3-heterocyclylprop-1-yl, 1-heterocyclylbut-1-yl, 2-heterocyclylbut-1-yl, 3-heterocyclylbut-1-yl, 4-heterocyclylbut-1-yl, 1-heterocyclylbut-2-yl, 2-heterocyclylbut-2-yl, 3-heterocyclylbut-2-yl, 4-heterocyclylbut-2-yl, 1-(heterocyclylmethyl)eth-1-yl, 1-(heterocyclylmethyl)-1-(methyl)eth-1-yl or 1-(heterocyclylmethyl)prop-1-yl, preferably heterocyclylmethyl or 2-heterocyclylethyl;

$C_1$–$C_4$-alkoxy: $OCH_3$, $OC_2H_5$, $OCH_2$—$C_2H_5$, $OCH(CH_3)_2$, n-butoxy, $OCH(CH_3)$—$C_2H_5$, $OCH_2$—$CH(CH_3)_2$ or $C(CH_3)_3$, preferably $OCH_3$, $OC_2H_5$ or $OCH(CH_3)_2$;

$C_1$–$C_4$-haloalkoxy: a $C_1$–$C_4$-alkoxy radical as mentioned above which is partially or fully substituted by fluorine, chlorine, bromine and/or iodine, i.e. for example $OCH_2Cl$, $OCH(Cl)_2$, $OC(Cl)_3$, $OCH_2F$, $OCHF_2$, $OCF_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, $OCF_2$—$C_2F_5$, 1-$(CH_2F)$-2-fluoroethoxy, 1-$(CH_2Cl)$-2-chloroethoxy, 1-$(CH_2Br)$-2-bromoethoxy, 4-fluorobutoxy, 4-chlorobutoxy, 4-bromobutoxy or nonafluorobutoxy, preferably $OCHF_2$, $OCF_3$, dichlorofluoromethoxy, chlorodifluoromethoxy or 2,2,2-trifluoroethoxy;

$C_1$–$C_6$-alkoxy: $C_1$–$C_4$-alkoxy as mentioned above, and also, for example, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, in particular $OCH_3$, $OC_2H_5$, $OCH(CH_3)_2$ or $OC(CH_3)_3$;

$C_1$–$C_6$-haloalkoxy: $C_1$–$C_6$-alkoxy as mentioned above which is partially or fully substituted by fluorine, chlorine, bromine and/or iodine, i.e. for example $OCH_2Cl$, $OCH(Cl)_2$, $OC(Cl)_3$, $OCH_2F$, $OCHF_2$, $OCF_3$, $OCHFCl$, $OCF(Cl)_2$, $OCF_2Cl$, $OCF_2Br$, 1-fluoroethoxy, 2-fluoroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluorethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-$(CH_2F)$-2-fluoroethoxy, 1-$(CH_2Cl)$-2-chloroethoxy, 1$CH_2Br)$-2-bromoethoxy, 4-fluorobutoxy, 4-chlorobutoxy, 4-bromobutoxy, nonafluorobutoxy, 5-fluoropentoxy, 5-chloropentoxy, 5-bromopentoxy, 5-iodopentoxy, 5,5,5-trichloropentoxy, undecafluoropentoxy, 6-fluorohexoxy, 6-chlorohexoxy, 6-bromohexoxy, 6,6,6-trichlorohexoxy or dodecafluorohexoxy;

$C_1$–$C_4$-alkylthio: $SCH_3$, $SC_2H_5$, $SCH_2$—$C_2H_5$, $SCH(CH_3)_2$, n-butylthio, 1-methylpropylthio, 2-methylpropylthio or $SC(CH_3)_3$, preferably $SCH_3$ or $SC_2H_5$;

$C_1$–$C_4$-haloalkylthio: a $C_1$–$C_4$-alkylthio radical as mentioned above which is partially or fully substituted by fluorine, chlorine, bromine and/or iodine, ie. for example $SCH_2Cl$, dichloromethylthio, trichloromethylthio, $SCH_2F$, difluoromethylthio, $SCF_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, $SC_2F_5$, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, 2,2,3,3,3-pentafluoropropylthio, $SCF_2$—$C_2F_5$, 1-$(CH_2F)$-2-fluoroethylthio, 1-$(CH_2Cl)$-2-chloroethylthio, 1-$(CH_2Br)$-2-bromoethylthio, 4-fluorobutylthio, 4-chlorobutylthio, 4-bromobutylthio or $SCF_2$—$CF_2$—$C_2F_5$, preferably $SCHF_2$, $SCF_3$, dichlorofluoromethylthio, chlorodifluoromethylthio or 2,2,2-trifluoroethylthio;

$C_1$–$C_6$-alkylthio: $C_1$–$C_4$-alkylthio as mentioned above, and also, for example, n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio, in particular $SCH_3$ or $SC_2H_5$;

$C_1$–$C_6$-haloalkylthio: a $C_1$–$C_6$-alkylthio radical as mentioned above which is partially or fully substituted by fluorine, chlorine, bromine and/or iodine, i.e. for example $SCH_2F$, $SCHF_2$, $SCF_3$, $SCH_2Cl$, $SCH(Cl)_2$, $SC(Cl)_3$, $SCHFCl$, $SCF(Cl)_2$, $SCF_2Cl$, $SCF_2Br$, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, $SC_2F_5$, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-$(CH_2F)$-2-fluoroethylthio, 1-$(CH_2Cl)$-2-chloroethylthio, 1-$(CH_2Br)$-2-bromoethylthio, 4-fluorobutylthio, 4-chlorobutylthio, 4-bromobutylthio, 5-fluoropentylthio, 5-chloropentylthio, 5-bromopentylthio, 5-iodopentylthio, 5,5,5-trichloropentylthio, undecafluoropentylthio, 6-fluorohexylthio, 6-chlorohexylthio, 6-bromohexylthio, 6,6,6-trichlorohexylthio or dodecafluorohexylthio, in particular $SCHF_2$, $SCF_3$ or $SC(Cl)_3$;

$C_1$–$C_4$-alkoxy-$C_1$–$C_4$-alkyl: $C_1$–$C_4$-alkyl which is substituted by $C_1$–$C_4$-alkoxy as mentioned above, ie. for example $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, preferably $CH_2$—$OCH_3$, $CH_2$—$OC_2H_5$, 2-methoxyethyl or 2-ethoxyethyl;

$C_1$–$C_4$-haloalkoxy-$C_1$–$C_4$-alkyl: $C_1$–$C_4$-alkyl which is substituted by $C_1$–$C_4$-haloalkoxy as mentioned above, ie. for example 2-(difluoromethoxy)ethyl, 2-(trifluoromethoxy)ethyl or 2-(pentafluoroethoxy)ethyl;

$C_1$–$C_4$-alkylthio-$C_1$–$C_4$-alkyl: $C_1$–$C_4$-alkyl which is substituted by $C_1$–$C_4$-alkylthio as mentioned above, ie. for example $CH_2$—$SCH_3$, $CH_2$—$SC_2H_5$, n-propylthiomethyl, $CH_2$—$SCH(CH_3)_2$, n-butylthiomethyl, (1-methylpropylthio)methyl, (2-methylpropylthio)methyl, $CH_2$—$SC(CH_3)_3$, 2-(methylthio)ethyl, 2-(ethylthio)ethyl, 2-(n-propylthio)ethyl, 2-(1-methylethylthio)ethyl, 2-(n-butylthio)ethyl, 2-(1-methylpropylthio)ethyl, 2-(2-methylpropylthio)ethyl, 2-(1,1-dimethylethylthio)ethyl, 2-(methylthio)propyl, 2-(ethylthio)propyl, 2-(n-propylthio)propyl, 2-(1-methylethylthio)propyl, 2-(n-butylthio)propyl, 2-(1-methylpropylthio)propyl, 2-(2-methylpropylthio)propyl, 2-(1,1-dimethylethylthio)propyl, 3-(methylthio)propyl, 3-(ethylthio)propyl, 3-(n-propylthio)propyl, 3-(1-methylethylthio)propyl, 3-(n-butylthio)propyl, 3-(1-methylpropylthio)propyl, 3-(2-methylpropylthio)propyl, 3-(1,1-dimethylethylthio)propyl, 2-(methylthio)butyl, 2-(ethylthio)butyl, 2-(n-propylthio)butyl, 2-(1-methylethylthio)butyl, 2-(n-butylthio)butyl, 2-(1-methylpropylthio)butyl, 2-(2-methylpropylthio)butyl, 2-(1,1-dimethylethylthio)butyl, 3-(methylthio)butyl, 3-(ethylthio)butyl, 3-(n-propylthio)butyl, 3-(1-methylethylthio)butyl, 3-(n-butylthio)butyl, 3-(1-methylpropylthio)butyl, 3-(2-methylpropylthio)butyl, 3-(1,1-dimethylethylthio)butyl, 4-(methylthio)butyl, 4-(ethylthio)butyl, 4-(n-propylthio)butyl, 4-(1-methylethylthio)butyl, 4-(n-butylthio)butyl, 4-(1-methylpropylthio)butyl, 4-(2-methylpropylthio)butyl or 4-(1,1-dimethylethylthio)butyl, preferably $CH_2$—$SCH_3$, $CH_2$—$SC_2H_5$, 2-(methylthio)ethyl or 2-(ethylthio)ethyl;

$C_1$–$C_4$-haloalkylthio-$C_1$–$C_4$-alkyl: $C_1$–$C_4$-alkyl which is substituted by $C_1$–$C_4$-haloalkylthio as mentioned above, ie. for example 2-(difluoromethylthio)ethyl, 2-(trifluoromethylthio)ethyl or 2-(pentafluoroethylthio)ethyl;

($C_1$–$C_4$-alkyl)carbonyl: $CO$—$CH_3$, $CO$—$C_2H_5$, $CO$—$CH_2$—$C_2H_5$, $CO$—$CH(CH_3)_2$, n-butylcarbonyl, $CO$—$CH(CH_3)$—$C_2H_5$, $CO$—$CH_2$—$CH(CH_3)_2$ or $CO$—$C(CH_3)_3$, preferably $CO$—$CH_3$ or $CO$—$C_2H_5$;

($C_1$–$C_4$-haloalkyl)carbonyl: a ($C_1$–$C_4$-alkyl)carbonyl radical as mentioned above which is partially or fully substituted by fluorine, chlorine, bromine and/or iodine, ie. for example $CO$—$CH_2Cl$, dichloromethylcarbonyl, trichloromethylcarbonyl, $CO$—$CH_2F$, $CO$—$CHF_2$, $CO$—$CF_3$, chlorofluoromethylcarbonyl, dichlorofluoromethylcarbonyl, chlorodifluoromethylcarbonyl, 2-fluoroethylcarbonyl, 2-chloroethylcarbonyl, 2-bromoethylcarbonyl, 2-iodoethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 2,2,2-trichloroethylcarbonyl, $CO$—$C_2F_5$, 2-fluoropropylcarbonyl, 3-fluoropropylcarbonyl, 2,2-difluoropropylcarbonyl, 2,3-difluoropropylcarbonyl, 2-chloropropylcarbonyl, 3-chloropropylcarbonyl, 2,3-dichloropropylcarbonyl, 2-bromopropylcarbonyl, 3-bromopropylcarbonyl, 3,3,3-trifluoropropylcarbonyl, 3,3,3-trichloropropylcarbonyl, 2,2,3,3,3-pentafluoropropylcarbonyl, heptafluoropropylcarbonyl, 1-($CH_2F$)-2-fluoroethylcarbonyl, 1-($CH_2Cl$)-2-chloroethylcarbonyl, 1-($CH_2Br$)-2-bromoethylcarbonyl, 4-fluorobutylcarbonyl, 4-chlorobutylcarbonyl, 4-bromobutylcarbonyl or nonafluorobutylcarbonyl, preferably $CO$—$CH_2Cl$, $CO$—$CF_3$ or 2,2,2-trifluoroethylcarbonyl;

($C_1$–$C_4$-alkyl)carbonyloxy: $O$—$CO$—$CH_3$, $O$—$CO$—$C_2H_5$, $O$—$CO$—$CH_2$—$C_2H_5$, $O$—$CO$—$CH(CH_3)_2$, $O$—$CO$—$CH_2$—$CH_2$—$C_2H_5$, $O$—$CO$—$CH(CH_3)$—$C_2H_5$, $O$—$CO$—$CH_2$—$CH(CH_3)_2$ or $O$—$CO$—$C(CH_3)_3$, preferably $O$—$CO$—$CH_3$ or $O$—$CO$—$C_2H_5$;

($C_1$–$C_4$-haloalkyl)carbonyloxy: a ($C_1$–$C_4$-alkyl)carbonyl radical as mentioned above which is partially or fully substituted by fluorine, chlorine, bromine and/or iodine, ie. for example $O$—$CO$—$CH_2Cl$, dichloromethylcarbonyloxy, trichloromethylcarbonyloxy, $O$—$CO$—$CH_2F$, $O$—$CO$—$CHF_2$, $O$—$CO$—$CF_3$, chlorofluoromethylcarbonyloxy, dichlorofluoromethylcarbonyloxy, chlorodifluoromethylcarbonyloxy, 2-fluoroethylcarbonyloxy, 2-chloro ethylcarbonyloxy, 2-bromoethylcarbonyloxy, 2-iodoethylcarbonyloxy, 2,2-difluoroethylcarbonyloxy, 2,2,2-trifluoroethylcarbonyloxy, 2-chloro-2-fluoroethylcarbonyloxy, 2-chloro-2,2-difluoroethylcarbonyloxy, 2,2-dichloro-2-fluoroethylcarbonyloxy, 2,2,2-trichloroethylcarbonyloxy, $O$—$CO$—$C_2F_5$, 2-fluoropropylcarbonyloxy, 3-fluoropropylcarbonyloxy, 2,2-difluoropropylcarbonyloxy, 2,3-difluoropropylcarbonyloxy, 2-chloropropylcarbonyloxy, 3-chloropropylcarbonyloxy, 2,3-dichloropropylcarbonyloxy, 2-bromopropylcarbonyloxy, 3-bromopropylcarbonyloxy, 3,3,3-trifluoropropylcarbonyloxy, 3,3,3-trichloropropylcarbonyloxy, 2,2,3,3,3-pentafluoropropylcarbonyloxy, heptafluoropropylcarbonyloxy, 1-($CH_2F$)-2-fluoroethylcarbonyloxy, 1-($CH_2Cl$)-2-chloroethylcarbonyloxy, 1-($CH_2Br$)-2-bromoethylcarbonyloxy, 4-fluorobutylcarbonyloxy, 4-chlorobutylcarbonyloxy, 4-bromobutylcarbonyloxy or nonafluorobutylcarbonyloxy, preferably $O$—$CO$—$CH_2Cl$, $O$—$CO$—$CF_3$ or 2,2,2-trifluoroethylcarbonyloxy;

($C_1$–$C_4$-alkoxy)carbonyl: $CO$—$OCH_3$, $CO$—$OC_2H_5$, n-propoxycarbonyl, $CO$—$OCH(CH_3)_2$, n-butoxycarbonyl, $CO$—$OCH(CH_3)$—$C_2H_5$, $CO$—$OCH_2$—$CH(CH_3)_2$ or $CO$—$OC(CH_3)_3$, preferably $CO$—$OCH_3$ or $CO$—$OC_2H_5$;

($C_1$–$C_4$-alkoxy)carbonyl-$C_1$–$C_4$-alkyl: $C_1$–$C_4$-alkyl which is substituted by ($C_1$–$C_4$-alkoxy)carbonyl as mentioned above, ie. for example CH$_2$—CO—OCH$_3$, CH$_2$—CO—OC$_2$H$_5$, n-propoxycarbonylmethyl, CH$_2$—CO—OCH(CH$_3$)$_2$, n-butoxycarbonylmethyl, CH$_2$—CO—OCH(CH$_3$)—C$_2$H$_5$, CH$_2$—CO—OCH$_2$—CH(CH$_3$)$_2$, CH$_2$—CO—OC(CH$_3$)$_3$, 1-(methoxycarbonyl)ethyl, 1-(ethoxycarbonyl)ethyl, 1-(n-propoxycarbonyl)ethyl, 1-(1-methylethoxycarbonyl)ethyl, 1-(n-butoxycarbonyl)ethyl, 2-(methoxycarbonyl)ethyl, 2-(ethoxycarbonyl)ethyl, 2-(n-propoxycarbonyl)ethyl, 2-(1-methylethoxycarbonyl)ethyl, 2-(n-butoxycarbonyl)ethyl, 2-(1-methylpropoxycarbonyl)ethyl, 2-(2-methylpropoxycarbonyl)ethyl, 2-(1,1-dimethylethoxycarbonyl)ethyl, 2-(methoxycarbonyl)propyl, 2-(ethoxycarbonyl)propyl, 2-(n-propoxycarbonyl)propyl, 2-(1-methylethoxycarbonyl)propyl, 2-(n-butoxycarbonyl)propyl, 2-(1-methylpropoxycarbonyl)propyl, 2-(2-methylpropoxycarbonyl)propyl, 2-(1,1-dimethylethoxycarbonyl)propyl, 3-(methoxycarbonyl)propyl, 3-(ethoxycarbonyl)propyl, 3-(n-propoxycarbonyl)propyl, 3-(1-methylethoxycarbonyl)propyl, 3-(n-butoxycarbonyl)propyl, 3-(1-methylpropoxycarbonyl)propyl, 3-(2-methylpropoxycarbonyl)propyl, 3-(1,1-dimethylethoxycarbonyl)propyl, 2-(methoxycarbonyl)butyl, 2-(ethoxycarbonyl)butyl, 2-(n-propoxycarbonyl)butyl, 2-(1-methylethoxycarbonyl)butyl, 2-(n-butoxycarbonyl)butyl, 2-(1-methylpropoxycarbonyl)butyl, 2-(2-methylpropoxycarbonyl)butyl, 2-(1,1-dimethylethoxycarbonyl)butyl, 3-(methoxycarbonyl)butyl, 3-(ethoxycarbonyl)butyl, 3-(n-propoxycarbonyl)butyl, 3-(1-methylethoxycarbonyl)butyl, 3-(n-butoxycarbonyl)butyl, 3-(1-methylpropoxycarbonyl)butyl, 3-(2-methylpropoxycarbonyl)butyl, 3-(1,1-dimethylethoxycarbonyl)butyl, 4-(methoxycarbonyl)butyl, 4-(ethoxycarbonyl)butyl, 4-(n-propoxycarbonyl)butyl, 4-(1-methylethoxycarbonyl)butyl, 4-(n-butoxycarbonyl)butyl, 4-(1-methylpropoxycarbonyl)butyl, 4-(2-methylpropoxycarbonyl)butyl or 4-(1,1-dimethylethoxycarbonyl)butyl, preferably CH$_2$—CO—OCH$_3$, CH$_2$—CO—OC$_2$H$_5$, 1-(methoxycarbonyl)ethyl or 1-(ethoxycarbonyl)ethyl;

($C_1$–$C_6$-alkoxy)carbonyl: ($C_1$–$C_4$-alkoxy)carbonyl as mentioned above, and also, for example, pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-C$_2$H$_5$-1—CH$_3$-propoxycarbonyl or 1-C$_2$H$_5$-2—CH$_3$-propoxycarbonyl, in particular COOCH$_3$, COOC$_2$H$_5$ or COOC(CH$_3$)$_3$;

($C_1$–$C_6$-alkoxy)carbonyl-$C_1$–$C_6$-alkoxy: ($C_1$–$C_6$-alkoxy) which is substituted by ($C_1$–$C_6$-alkoxy)carbonyl as mentioned above, i.e. for example OCH$_2$COOCH$_3$, OCH$_2$COOC$_2$H$_5$, OCH$_2$COOCH$_2$—C$_2$H$_5$, OCH$_2$COOCH(CH$_3$)$_2$, OCH$_2$COOCH$_2$CH$_2$—C$_2$H$_5$, (1-methylpropoxycarbonyl)-methoxy, (2-methylpropoxycarbonyl)methoxy, OCH$_2$COOC(CH$_3$)$_3$, OCH$_2$COO(CH$_2$)$_3$—C$_2$H$_5$, OCH$_2$COO(CH$_2$)$_4$—C$_2$H$_5$, OCH(CH$_3$)COOCH$_3$, OCH(CH$_3$)COOC$_2$H$_5$, OCH$_2$CH$_2$COOCH$_3$, OCH$_2$CH$_2$COOC$_2$H$_5$, OCH$_2$CH$_2$COOCH$_2$—C$_2$H$_5$, OCH$_2$CH$_2$COOCH(CH$_3$)$_2$, OCH$_2$CH$_2$COOCH$_2$CH$_2$—C$_2$H$_5$, 2-(1-methylpropoxycarbonyl)ethoxy, 2-(2-methylpropoxycarbonyl)ethoxy, OCH$_2$CH$_2$COOC(CH$_3$)$_3$, OCH$_2$CH$_2$COO(CH$_2$)$_3$—C$_2$H$_5$, OCH$_2$CH$_2$COO(CH$_2$)$_4$—C$_2$H$_5$, 2—(COOCH$_3$)propoxy, 2-[COOCH(CH$_3$)$_2$]propoxy, 2-(COOCH$_2$CH$_2$—C$_2$H$_5$)propoxy, 2-(1-methylpropoxycarbonyl)propoxy, 2-(2-methylpropoxycarbonyl)propoxy, 2-[COOC(CH$_3$)$_3$]propoxy, 3-(COOCH$_3$)propoxy, 3-(COOC$_2$H$_5$)propoxy, 3-(COOCH$_2$—C$_2$H$_5$)propoxy, 3-[COOCH(CH$_3$)$_2$]propoxy, 3-(COOCH$_2$CH$_2$—C$_2$H$_5$)propoxy, 3-(1-methylpropoxycarbonyl)propoxy, 3-(2-methylpropoxycarbonyl)propoxy, 3-[COOC(CH$_3$)3]propoxy, 3-[COO(CH$_2$)$_3$—C$_2$H$_5$]propoxy, 3-[COO(CH$_2$)$_4$—C$_2$H$_5$]propoxy, 2-(COOCH$_3$)butoxy, 2-(COOC$_2$H$_5$)butoxy, 2-(COOCH$_2$—C$_2$H$_5$)butoxy, 2-[COOCH(CH$_3$)$_2$]butoxy, 2-(COOCH$_2$CH$_2$—C$_2$H$_5$)butoxy, 2-(1-methylpropoxycarbonyl)butoxy, 2-(2-methylpropoxycarbonyl)butoxy, 2-[COOC(CH$_3$)3]butoxy, 3-(COOCH$_3$)butoxy, 3-(COOC$_2$H$_5$)butoxy, 3-(COOCH$_2$—C$_2$H$_5$)butoxy, 3-[COOCH(CH$_3$)$_2$]butoxy, 3-(COOCH$_2$CH$_2$—C$_2$H$_5$)butoxy, 3-(1-methylpropoxycarbonyl)butoxy, 3-(2-methylpropoxycarbonyl)butoxy, 3-[COOC(CH$_3$)$_3$]butoxy, 4-(COOCH$_3$)butoxy, 4-(COOC$_2$H$_5$)butoxy, 4-(COOCH$_2$—C$_2$H$_5$)butoxy, 4-[COOCH(CH$_3$)$_2$]butoxy, 4-(COOCH$_2$CH$_2$—C$_2$H$_5$)butoxy, 4-(1-methylpropoxycarbonyl)butoxy, 4-(2-methylpropoxycarbonyl)butoxy, 4-[COOC(CH$_3$)$_3$]butoxy, 4-[COO(CH$_2$)$_3$—C$_2$H$_5$]butoxy, 4-[COO(CH$_2$)$_4$—C$_2$H$_5$]butoxy, 5-(COOCH$_3$)pentoxy, 5-(COOC$_2$H$_5$)pentoxy, 5-(COOCH$_2$—C$_2$H$_5$)pentoxy, 5-[COOCH(CH$_3$)$_2$]pentoxy, 5-(COOCH$_2$CH$_2$—C$_2$H$_5$)pentoxy, 5-(1-methylpropoxycarbonyl)pentoxy, 5-(2-methylpropoxycarbonyl)pentoxy, 5-[COOC(CH$_3$)$_3$]pentoxy, 5-[COO(CH$_2$)$_3$—C$_2$H$_5$]pentoxy, 5-[COO(CH$_2$)$_4$—C$_2$H$_5$]pentoxy, 6-(COOCH$_3$)hexoxy, 6-(COOC$_2$H$_5$)hexoxy, 6-(COOCH$_2$—C$_2$H$_5$)hexoxy, 6-[COOCH(CH$_3$)$_2$]hexoxy, 6-(COOCH$_2$CH$_2$—C$_2$H$_5$)hexoxy, 6-(1-methylpropoxycarbonyl)hexoxy, 6-(2-methylpropoxycarbonyl)hexoxy, 6-[COOC(CH$_3$)$_3$]hexoxy, 6-[COO(CH$_2$)$_3$—C$_2$H$_5$]hexoxy or 6-[COO(CH$_2$)$_4$—C$_2$H$_5$]hexoxy, in particular OCH$_2$COOCH$_3$, OCH$_2$COOCH(CH$_3$)$_2$, OCH(CH$_3$)COOCH$_3$ oder OCH$_2$CH$_2$COOCH$_3$;

($C_1$–$C_4$-alkylthio)carbonyl: CO—SCH$_3$, CO—SC$_2$H$_5$, CO—SCH$_2$—C$_2$H$_5$, CO—SCH(CH$_3$)$_2$, CO—SCH$_2$CH$_2$—C$_2$H$_5$, CO—SCH(CH$_3$)—C$_2$H$_5$, CO—SCH$_2$—CH(CH$_3$)$_2$ or CO—SC(CH$_3$)$_3$, preferably CO—SCH$_3$ or CO—SC$_2$H$_5$;

($C_1$–$C_4$-alkylthio)carbonyl-$C_1$–$C_4$-alkyl: $C_1$–$C_4$-alkyl which is substituted by ($C_1$–$C_4$-alkylthio)carbonyl—as mentioned above—ie. for example CH$_2$—CO—SCH$_3$, CH$_2$–CO—SC$_2$H$_5$, CH$_2$-CO—SCH$_2$-C$_2$H$_5$, CH$_2$—CO—SCH(CH$_3$)$_2$, CH$_2$—CO—SCH$_2$CH$_2$—C$_2$H$_5$, CH$_2$—CO—SCH(CH$_3$)—C$_2$H$_5$CH$_2$—CO—SCH$_2$—CH(CH$_3$)$_2$, CH$_2$—CO—SC(CH$_3$)$_3$, 1-(CO—SCH$_3$)ethyl, 1-(CO—SC$_2$H$_5$)ethyl, 1-(CO—SCH$_2$—C$_2$H$_5$)

ethyl, 1-[CO—SCH(CH$_3$)$_2$]ethyl, 1-(CO—SCH$_2$CH$_2$—C$_2$H$_5$)ethyl, 1-[CO—SCH(CH$_3$)—C$_2$H$_5$]ethyl, 1-[CO—SCH$_2$—CH(CH$_3$)$_2$]ethyl, 1-[CO—SC(CH$_3$)$_3$]ethyl, 2-(CO—SCH$_3$)ethyl, 2-(CO—SC$_2$H$_5$)ethyl, 2-(CO—SCH$_2$—C$_2$H$_5$)ethyl, 2-[CO—SCH(CH$_3$)$_2$]ethyl, 2-(CO—SCH$_2$CH$_2$—C$_2$H$_5$)ethyl, 2-[CO—SCH(CH$_3$)—C$_2$H$_5$]ethyl, 2-[CO—SCH$_2$—CH(CH$_3$)$_2$]ethyl, 2-[CO—SC(CH$_3$)$_3$]ethyl, 2-(CO—SCH$_3$)propyl, 2-(CO—SC$_2$H$_5$)propyl, 2-(CO—SCH$_2$—C$_2$H$_5$)propyl, 2-[CO—SCH(CH$_3$)$_2$]propyl, 2-(CO—SCH$_2$CH$_2$—C$_2$H$_5$)propyl, 2-[CO—SCH(CH$_3$)—C$_2$H$_5$]propyl, 2-[CO—SCH$_2$—CH(CH$_3$)$_2$]propyl, 2-[CO—SC(CH$_3$)$_3$]propyl, 3-(CO—SCH$_3$)propyl, 3-(CO—SC$_2$H$_5$)propyl, 3-(CO—SCH$_2$—C$_2$H$_5$)propyl, 3-[CO—SCH(CH$_3$)$_2$]propyl, 3-(CO—SCH$_2$CH$_2$—C$_2$H$_5$)propyl, 3-[CO—SCH(CH$_3$)—C$_2$H$_5$]propyl, 3-[CO—SCH$_2$—CH(CH$_3$)$_2$]propyl, 3-[CO—SC(CH$_3$)$_3$]propyl, 2-(CO—SCH$_3$)butyl, 2-(CO—SC$_2$H$_5$)butyl, 2-(CO—SCH$_2$—C$_2$H$_5$)butyl, 2-[CO—SCH(CH$_3$)$_2$]butyl, 2-(CO—SCH$_2$CH$_2$—C$_2$H$_5$)butyl, 2-[CO—SCH(CH$_3$)—C$_2$H$_5$]butyl, 2-[CO—SCH$_2$—CH(CH$_3$)$_2$]butyl, 2-[CO—SC(CH$_3$)$_3$]butyl, 3-(CO—SCH$_3$)butyl, 3-(CO—SC$_2$H$_5$)butyl, 3-(CO—SCH$_2$—C$_2$H$_5$)butyl, 3-[CO—SCH(CH$_3$)$_2$]butyl, 3-(CO—SCH$_2$CH$_2$—C$_2$H$_5$)butyl, 3-[CO—SCH(CH$_3$)—C$_2$H$_5$]butyl, 3-[CO—SCH$_2$—CH(CH$_3$)$_2$]butyl, 3-[CO—SC(CH$_3$)$_3$]butyl, 4-(CO—SCH$_3$)butyl, 4-(CO—SC$_2$H$_5$)butyl, 4-(CO—SCH$_2$—C$_2$H$_5$)butyl, 4-[CO—SCH(CH$_3$)$_2$]butyl, 4-(CO—SCH$_2$CH$_2$—C$_2$H$_5$)butyl, 4-[CO—SCH(CH$_3$)—C$_2$H$_5$]butyl, 4-[CO—SCH$_2$—CH(CH$_3$)$_2$]butyl or 4-[CO—SC(CH$_3$)$_3$]butyl, preferably CH$_2$—CO—SCH$_3$, CH$_2$—CO—SC$_2$H$_5$, 1-(CO—SCH$_3$)ethyl or 1-(CO—SC$_2$H$_5$)ethyl;

$C_1$–$C_6$-alkylsulfinyl: SO—CH$_3$, SO—C$_2$H$_5$, SO—CH$_2$—C$_2$H$_5$, SO—CH(CH$_3$)$_2$, n-butylsulfinyl, SO—CH(CH$_3$)—C$_2$H$_5$, SO—CH$_2$—CH(CH$_3$)$_2$, SO—C(CH$_3$)$_3$, n-pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, n-hexylsulfinyl, 1,1-dimethylpropylsulfinyl, 1,2-dimethylpropylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl, in particular SOCH$_3$ or SOC$_2$H$_5$;

$C_1$–$C_6$-haloalkylsulfinyl: a $C_1$–$C_6$-alkylsulfinyl radical—as mentioned above—which is partially or fully substituted by fluorine, chlorine, bromine and/or iodine, i.e. for example SO—CH$_2$F, SO—CHF$_2$, SO—CF$_3$, SO—CH$_2$Cl, SO—CH(Cl)$_2$, SO—C(Cl)$_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl, SO—C$_2$F$_5$, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, 5,5,5-trichloropentylsulfinyl, undecafluoropentylsulfinyl, 6-fluorohexylsulfinyl, 6-chlorohexylsulfinyl, 6-bromohexylsulfinyl, 6-iodohexylsulfinyl, 6,6,6-trichlorohexylsulfinyl or dodecafluorohexylsulfinyl, preferably SO—CH$_2$Cl, SO—CF$_3$ or 2,2,2-trifluoroethylsulfinyl;

$C_1$–$C_4$-alkylsulfinyl-$C_1$–$C_4$-alkyl: $C_1$–$C_4$-alkyl which is substituted by $C_1$–$C_4$-alkylsulfinyl as mentioned above, ie. for example CH$_2$SOCH$_3$, CH$_2$SOC$_2$H$_5$, n-propylsulfinylmethyl, (1-methylethylsulfinyl)methyl, n-butylsulfinylmethyl, (1-methylpropylsulfinyl)methyl, (2-methylpropylsulfinyl)methyl, (1,1-dimethylethylsulfinyl)methyl, 2-methylsulfinylethyl, 2-ethylsulfinylethyl, 2-(n-propylsulfinyl)ethyl, 2-(1-methylethylsulfinyl)-ethyl, 2-(n-butylsulfinyl)ethyl, 2-(1-methylpropylsulfinyl)ethyl, 2-(2-methylpropylsulfinyl)-ethyl, 2-(1,1-dimethylethylsulfinyl)ethyl, 2-(SOCH$_3$)propyl, 3-(SOCH$_3$)propyl, 2-(SOC$_2$H$_5$)propyl, 3-(SOC$_2$H$_5$)propyl, 3-(propylsulfinyl)propyl, 3-(butylsulfinyl)propyl, 4-(SOCH$_3$)butyl, 4-(SOC$_2$H$_5$)butyl, 4-(n-propylsulfinyl)butyl or 4-(n-butylsulfinyl)butyl, in particular 2-(SOCH$_3$)ethyl;

$C_1$–$C_4$-haloalkylsulfinyl-$C_1$–$C_4$-alkyl: $C_1$–$C_4$-alkyl which is substituted by $C_1$–$C_4$-haloalkylsulfinyl as mentioned above, ie. for example 2-(2,2,2-trifluoroethylsulfinyl)ethyl;

$C_1$–$C_4$-alkylsulfonyl: SO$_2$—CH$_3$, SO$_2$—C$_2$H$_5$, SO$_2$—CH$_2$—C$_2$H$_5$, SO$_2$—CH(CH$_3$)$_2$, n-butylsulfonyl, SO$_2$—CH(CH$_3$)—C$_2$H$_5$, SO$_2$—CH$_2$—CH(CH$_3$) or SO$_2$—C(CH$_3$)$_3$, preferably SO$_2$—CH$_3$ or SO$_2$—C$_2$H$_5$;

$C_1$–$C_4$-haloalkylsulfonyl: a $C_1$–$C_4$-alkylsulfonyl radical as mentioned above which is partially or fully substituted by fluorine, chlorine, bromine and/or iodine, ie. for example SO$_2$—CH$_2$F, SO$_2$—CHF$_2$, SO$_2$—CF$_3$, SO$_2$—CH$_2$Cl, SO$_2$—CH(Cl)$_2$, SO$_2$—C(Cl)$_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, SO$_2$—C$_2$F$_5$, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl or nonafluorobutylsulfonyl, preferably SO$_2$—CH$_2$Cl, SO$_2$—CF$_3$ or 2,2,2-trifluoroethylsulfonyl;

C$_1$–C$_6$-alkylsulfonyl: C$_1$–C$_4$-alkylsulfonyl as mentioned above, and also, for example, n-pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, n-hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl, in particular SO$_2$CH$_3$ or SO$_2$C$_2$H$_5$;

C$_1$–C$_6$-haloalkylsulfonyl: a C$_1$–C$_6$-alkylsulfonyl radical—as mentioned above—which is partially or fully substituted by fluorine, chlorine, bromine and/or iodine, i.e. for example one of the radicals mentioned under C$_1$–C$_4$-haloalkylsulfonyl, or 5-fluoropentylsulfonyl, 5-chloropentylsulfonyl, 5-bromopentylsulfonyl, 5-iodopentylsulfonyl, 5,5,5-trichloropentylsulfonyl, undecafluoropentylsulfonyl, 6-fluorohexylsulfonyl, 6-chlorohexylsulfonyl, 6-bromohexylsulfonyl, 6-iodohexylsulfonyl, 6,6,6-trichlorohexylsulfonyl or dodecafluorohexylsulfonyl;

C$_1$–C$_4$-alkylsulfonyl-C$_1$–C$_4$-alkyl: C$_1$–C$_4$-alkyl which is substituted by C$_1$–C$_4$-alkylsulfonyl as mentioned above, ie. for example CH$_2$SO$_2$—CH$_3$, CH$_2$SO$_2$—C$_2$H$_5$, CH$_2$SO$_2$—CH$_2$—C$_2$H$_5$, CH$_2$SO$_2$—CH(CH$_3$)$_2$, CH$_2$SO$_2$—CH$_2$CH$_2$—C$_2$H$_5$, (1-methylpropylsulfonyl)methyl, (2-methylpropylsulfonyl)methyl, CH$_2$SO$_2$—C(CH$_3$)$_3$, CH(CH$_3$)SO$_2$—CH$_3$, CH(CH$_3$)SO$_2$—C$_2$H$_5$, CH$_2$CH$_2$SO$_2$—CH$_3$, CH$_2$CH$_2$SO$_2$—C$_2$H$_5$, CH$_2$CH$_2$SO$_2$—CH$_5$, CH$_2$CH$_2$SO$_2$—CH(CH$_3$)$_2$, CH$_2$CH$_2$SO$_2$—CH$_2$CH$_2$—C$_2$H$_5$, 2-(1-methylpropylsulfonyl)ethyl, 2-(2-methylpropylsulfonyl)ethyl, CH$_2$CH$_2$SO$_2$—C(CH$_3$)$_3$, 2-(SO$_2$—CH$_3$)propyl, 2-(SO$_2$—C$_2$H$_5$)propyl, 2-(SO$_2$—CH$_2$—C$_2$H$_5$)propyl, 2-[SO$_2$—CH(CH$_3$)$_2$]propyl, 2-(SO$_2$—CH$_2$CH$_2$—C$_2$H$_5$)propyl, 2-(1-methylpropylsulfonyl)propyl, 2-(2-methylpropylsulfonyl)propyl, 2-[SO$_2$—C(CH$_3$)$_3$]propyl, 3-(SO$_2$—CH$_3$)propyl, 3-(SO$_2$—C$_2$H$_5$)propyl, 3-(SO$_2$—CH$_2$—C$_2$H$_5$)propyl, 3-[SO$_2$—CH(CH$_3$)$_2$]propyl, 3-(SO$_2$—CH$_2$CH$_2$—C$_2$H$_5$)propyl, 3-(1-methylpropylsulfonyl)propyl, 3-(2-methylpropylsulfonyl)propyl, 3-[SO$_2$—C(CH$_3$)$_3$]propyl, 2-(SO$_2$—CH$_3$)butyl, 2-(SO$_2$—C$_2$H$_5$)butyl, 2-(SO$_2$—CH$_2$—C$_2$H$_5$)butyl, 2-[SO$_2$—CH(CH$_3$)$_2$]butyl, 2-(SO$_2$—CH$_2$CH$_2$—C$_2$H$_5$)butyl, 2-(1-methylpropylsulfonyl)butyl, 2-(2-methylpropylsulfonyl)butyl, 2-[SO$_2$—C(CH$_3$)$_3$]butyl, 3-(SO$_2$—CH$_3$)butyl, 3-(SO$_2$—C$_2$H$_5$)butyl, 3-(SO$_2$—CH$_2$—C$_2$H$_5$)butyl, 3-[SO$_2$—CH(CH$_3$)$_2$]butyl, 3-(SO$_2$—CH$_2$CH$_2$—C$_2$H$_5$)butyl, 3-(1-methylpropylsulfonyl)butyl, 3-(2-methylpropylsulfonyl)butyl, 3-[SO$_2$—C(CH$_3$)$_3$]butyl, 4-(SO$_2$—CH$_3$)butyl, 4-(SO$_2$—C$_2$H$_5$)butyl, 4-(SO$_2$—CH$_2$—C$_2$H$_5$)butyl, 4-[SO$_2$—CH(CH$_3$)$_2$]butyl, 4-(SO$_2$—CH$_2$CH$_2$—C$_2$H$_5$)butyl, 4-(1-methylpropylsulfonyl)butyl, 4-(2-methylpropylsulfonyl)butyl or 4-[SO$_2$—C(CH$_3$)$_3$]butyl, in particular CH$_2$CH$_2$SO$_2$—CH$_3$ or CH$_2$CH$_2$SO$_2$—C$_2$H$_5$;

C$_1$–C$_4$-haloalkylsulfonyl-C$_1$–C$_4$-alkyl: C$_1$–C$_4$-alkyl which is substituted by C$_1$–C$_4$-haloalkylsulfonyl as mentioned above, ie. for example 2-(2,2,2-trifluoroethylsulfonyl)ethyl;

C$_1$–C$_4$-alkylamino-C$_1$–C$_4$-alkyl: C$_1$–C$_4$-alkyl which is substituted by C$_1$–C$_4$-alkylamino such as H$_3$C—NH—, H$_5$C$_2$—NH—, n-propyl-NH—, 1-methylethyl-NH—, n-butyl-NH—, 1-methylpropyl-NH—, 2-methylpropyl-NH— and 1,1-dimethylethyl-NH—, preferably H$_3$C—NH— or H$_3$C$_2$—NH—, ie. for example CH$_2$CH$_2$—NH—CH$_3$, CH$_2$CH$_2$—N(CH$_3$)$_2$, CH$_2$CH$_2$—NH—C$_2$H$_5$ or CH$_2$CH$_2$—N(C$_2$H$_5$)$_2$;

C$_1$–C$_4$-alkylaminocarbonyl: CO—NH—CH$_3$, CO—NH—C$_2$H$_5$, n-propylamino, CO—NH—CH(CH$_3$)$_2$, CO—NH—CH$_2$CH$_2$—C$_2$H$_5$, CO—NH—CH(CH$_3$)—C$_2$H$_5$, CO—NH—CH$_2$-CH(CH$_3$)$_2$ or CO—NH—C(CH$_3$)$_3$, preferably CO—NH—CH$_3$ or CO—NH—C$_2$H$_5$;

C$_1$–C$_4$-alkylaminocarbonyl-C$_1$–C$_4$-alkyl: C$_1$–C$_4$-alkyl which is substituted by C$_1$–C$_4$-alkylaminocarbonyl as mentioned above, preferably by CO—NH—CH$_3$ or CO—NH—C$_2$H$_5$, ie. for example CH$_2$—CO—NH—CH$_3$, CH$_2$—CO—NH—C$_2$H$_5$, CH$_2$—CO—NH—CH$_2$—C$_2$H$_5$, CH$_2$—CO—NH—CH(CH$_3$)$_2$, CH$_2$—CO—NH—CH$_2$CH$_2$—C$_2$H$_5$, CH$_2$—CO—NH—CH(CH$_3$)—C$_2$H$_5$, CH$_2$—CO—NH—CH$_2$—CH(CH$_3$)$_2$, CH$_2$—CO—NH—C(CH$_3$)$_3$, CH(CH$_3$)—CO—NH—CH$_3$, CH(CH$_3$)—CO—NH—C$_2$H$_5$, 2-(CO—NH—CH$_3$)ethyl, 2-(CO—NH—C$_2$H$_5$)ethyl, 2-(CO—NH—CH$_2$—C$_2$H$_5$)ethyl, 2-[CH$_2$—CO—NH—CH(CH$_3$)$_2$]ethyl, 2-(CO—NH—CH$_2$CH$_2$—C$_2$H$_5$)ethyl, 2-[CO—NH—CH(CH$_3$)—C$_2$H$_5$]ethyl, 2-[CO—NH—CH$_2$—CH(CH$_3$)$_2$]ethyl, 2-[CO—NH—C(CH$_3$)$_3$]ethyl, 2-(CO—NH—CH$_3$)propyl, 2-(CO—NH—C$_2$H$_5$) propyl, 2-(CO—NH—CH$_2$—C$_2$H$_5$)propyl, 2-[CH$_2$—CO—NH—CH(CH$_3$)$_2$]propyl, 2-(CO—NH—CH$_2$CH$_2$—C$_2$H$_5$)propyl, 2-[CO—NH—CH(CH$_3$)—C$_2$H$_5$]propyl, 2-[CO—NH—CH$_2$—CH(CH$_3$)$_2$]propyl, 2-[CO—NH—C(CH$_3$)$_3$]propyl, 3-(CO—NH—CH$_3$) propyl, 3-(CO—NH—C$_2$H$_5$)propyl, 3-(CO—NH—CH$_2$—C$_2$H$_5$)propyl, 3-[CH$_2$—CO—NH—CH(CH$_3$)$_2$]propyl, 3-(CO—NH—CH$_2$CH$_2$—C$_2$H$_5$)propyl, 3-[CO—NH—CH(CH$_3$)—C$_2$H$_5$]propyl, 3-[CO—NH—CH$_2$—CH(CH$_3$)$_2$]propyl, 3-[CO—NH—C(CH$_3$)$_3$]propyl, 2-(CO—NH—CH$_3$)butyl, 2-(CO—NH—C$_2$H$_5$)butyl, 2-(CO—NH—CH$_2$—C$_2$H$_5$)butyl, 2-[CH$_2$—CO—NH—CH(CH$_3$)$_2$]butyl, 2-(CO—NH—CH$_2$CH$_2$—C$_2$H$_5$)butyl, 2-[CO—NH—CH(CH$_3$)—C$_2$H$_5$]butyl, 2-[CO—NH—CH$_2$—CH(CH$_3$)$_2$]butyl, 2-[CO—NH—C(CH$_3$)$_3$]butyl, 3-(CO—NH—CH$_3$) butyl, 3-(CO—NH—C$_2$H$_5$)butyl, 3-(CO—NH—CH$_2$—C$_2$H$_5$)butyl, 3-[CH$_2$—CO—NH—CH(CH$_3$)$_2$] butyl, 3-(CO—NH—CH$_2$CH$_2$—C$_2$H$_5$)butyl, 3-[CO—NH—CH(CH$_3$)—C$_2$H$_5$]butyl, 3-[CO—NH—CH$_2$—CH(CH$_3$)$_2$]butyl, 3-[CO—NH—C(CH$_3$)$_3$]butyl, 4-(CO—NH—CH$_3$)butyl, 4-(CO—NH—C$_2$H$_5$)butyl, 4-(CO—NH—CH$_2$—C$_2$H$_5$)butyl, 4-[CH$_2$—CO—NH—CH(CH$_3$)$_2$]butyl, 4-(CO—NH—CH$_2$CH$_2$—C$_2$H$_5$)butyl, 4-[CO—NH—CH(CH$_3$)—C$_2$H$_5$]butyl, 4-[CO—NH—CH$_2$—CH(CH$_3$)$_2$]butyl or 4-[CO—NH—C(CH$_3$)$_3$]butyl, preferably CH$_2$—CO—NH—CH$_3$, CH$_2$—CO—NH—C$_2$H$_5$, CH(CH$_3$)—CO—NH—CH$_3$ or CH(CH$_3$)—CO—NH—C$_2$H$_5$;

C$_1$–C$_6$-alkylaminosulfonyl: for example H$_3$C—NHSO$_2$—, H$_5$C$_2$—NHSO$_2$—, n-propyl-NHSO$_2$—, (CH₃)₂CH—NHSO₂—, n-butyl-NHSO₂—, 1-methylpropyl-NHSO₂—, 2-methylpropyl-NHSO₂—, (CH₃)₃C—NHSO₂—, n-pentyl-NHSO₂—, 1-methylbutyl-NHSO₂—, 2-methylbutyl-NHSO₂—, 3-methylbutyl-NHSO₂—, 2,2-dimethylpropyl-NHSO₂—, 1-ethylpropyl-NHSO₂—, n-Hexyl-NHSO₂—, 1,1-dimethylpropyl-NHSO₂—, 1,2-dimethylpropyl-NHSO₂—, 1-methylpentyl-NHSO₂—, 2-methylpentyl-NHSO₂—, 3-methylpentyl-NHSO₂—, 4-methylpentyl-NHSO₂—, 1,1-dimethylbutyl-NHSO₂—, 1,2-dimethylbutyl-NHSO₂—, 1,3-dimethylbutyl-NHSO₂—, 2,2-dimethylbutyl-NHSO₂—, 2,3-dimethylbutyl-NHSO₂—, 3,3-dimethylbutyl-NHSO₂—, 1-ethylbutyl-NHSO₂—, 2-ethylbutyl-NHSO₂—, 1,1,2-trimethylpropyl-NHSO₂—, 1,2,2-trimethylpropyl-NHSO₂—, 1-ethyl-1-methylpropyl-NHSO₂— or 1-ethyl-2-methylpropyl-NHSO₂—, in particular H₃C—NHSO₂— or H₅C₂—NHSO₂—;

di(C₁–C₄-alkyl)amino: N(CH₃)₂, N(C₂H₅), N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino, preferably N(CH₃)₂ or N(C₂H₅);

di(C₁–C₄-alkyl)amino-C₁–C₄-alkyl: C₁–C₄-alkyl which is substituted by di(C₁–C₄-alkyl)amino as mentioned above, ie. for example CH₂N(CH₃)₂, CH₂N(C₂H₅)₂, N,N-dipropylaminomethyl, N,N-di(1-methylethyl)aminomethyl, N,N-dibutylaminomethyl, N,N-di(1-methylpropyl)aminomethyl, N,N-di(2-methylpropyl)-aminomethyl, N,N-di(1,1-dimethylethyl)aminomethyl, N-ethyl-N-methylaminomethyl, N-methyl-N-propylaminomethyl, N-methyl-N-(1-methylethyl)aminomethyl, N-butyl-N-methylaminomethyl, N-methyl-N-(1-methylpropyl)aminomethyl, N-methyl-N-(2-methylpropyl)aminomethyl, N-(1,1-dimethylethyl)-N-methylaminomethyl, N-ethyl-N-propylaminomethyl, N-ethyl-N-(1-methylethyl)aminomethyl, N-butyl-N-ethylaminomethyl, N-ethyl-N-(1-methylpropyl)-aminomethyl, N-ethyl-N-(2-methylpropyl)aminomethyl, N-ethyl-N-(1,1-dimethylethyl)aminomethyl, N-(1-methylethyl)-N-propylaminomethyl, N-butyl-N-propylaminomethyl, N-(1-methylpropyl)-N-propylaminomethyl, N-(2-methylpropyl)-N-propylaminomethyl, N-(1,1-dimethylethyl)-N-propylaminomethyl, N-butyl-N-(1-methylethyl)aminomethyl, N-(1-methylethyl)-N-(1-methylpropyl)aminomethyl, N-(1-methylethyl)-N-(2-methylpropyl)aminomethyl, N-(1,1-dimethylethyl)-N-(1-methylethyl)aminomethyl, N-butyl-N-(1-methylpropyl)aminomethyl, N-butyl-N-(2-methylpropyl)aminomethyl, N-butyl-N-(1,1-dimethylethyl)aminomethyl, N-(1-methylpropyl)-N-(2-methylpropyl)aminomethyl, N-(1,1-dimethylethyl)-N-(1-methylpropyl)aminomethyl, N-(1,1-dimethylethyl)-N-(2-methylpropyl)aminomethyl, N,N-dimethylaminoethyl, N,N-diethylaminoethyl, N,N-di(n-propyl)aminoethyl, N,N-di(1-methylethyl)aminoethyl, N,N-dibutylaminoethyl, N,N-di(1-methylpropyl)aminoethyl, N,N-di(2-methylpropyl)aminoethyl, N,N-di(1,1-dimethylethyl)aminoethyl, N-ethyl-N-methylaminoethyl, N-methyl-N-propylaminoethyl, N-methyl-N-(1-methylethyl)aminoethyl, N-butyl-N-methylaminoethyl, N-methyl-N-(1-methylpropyl)-aminoethyl, N-methyl-N-(2-methylpropyl)aminoethyl, N-(1,1-dimethylethyl)-N-methylaminoethyl, N-ethyl-N-propylaminoethyl, N-ethyl-N-(1-methylethyl)aminoethyl, N-butyl-N-ethylaminoethyl, N-ethyl-N-(1-methylpropyl)aminoethyl, N-ethyl-N-(2-methylpropyl)aminoethyl, N-ethyl-N-(1,1-dimethylethyl)-aminoethyl, N-(1-methylethyl)-N-propylaminoethyl, N-butyl-N-propylaminoethyl, N-(1-methylpropyl)-N-propylaminoethyl, N-(2-methylpropyl)-N-propylaminoethyl, N-(1,1-dimethylethyl)-N-propylaminoethyl, N-butyl-N-(1-methylethyl)aminoethyl, N-(1-methylethyl)-N-(1-methylpropyl)aminoethyl, N-(1-methylethyl)-N-(2-methylpropyl)aminoethyl, N-(1,1-dimethylethyl)-N-(1-methylethyl)aminoethyl, N-butyl-N-(1-methylpropyl)aminoethyl, N-butyl-N-(2-methylpropyl)aminoethyl, N-butyl-N-(1,1-dimethylethyl)aminoethyl, N-(1-methylpropyl)-N-(2-methylpropyl)aminoethyl, N-(1,1-dimethylethyl)-N-(1-methylpropyl)aminoethyl or N-(1,1-dimethylethyl)-N-(2-methylpropyl)aminoethyl, in particular N,N-dimethylaminoethyl or N,N-diethylaminoethyl;

di(C₁–C₄-alkyl)aminocarbonyl: CO—N(CH₃)₂, CO—N(C₂H₅), CO—N(CH₂—C₂H₅)₂, CO—N[CH(CH₃)₂]₂, N,N-dibutylaminocarbonyl, CO—N[CH(CH₃)—C₂H₅]₂, CO—N[CH₂—CH(CH₃)₂]₂, CO—N[C(CH₃)₃]₂, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl- N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl, preferably CO—N(CH$_3$)$_2$ or CO—N(C$_2$H$_5$);

di(C$_1$–C$_4$-alkyl)aminocarbonyl-C$_1$–C$_4$-alkyl: C$_1$–C$_4$-alkyl which is substituted by di(C$_1$–C$_4$-alkyl)aminocarbonyl as mentioned above, preferably by CO—N(CH$_3$)$_2$ or CO—N(C$_2$H$_5$)$_2$, ie. for example CH$_2$—CO—N(CH$_3$)$_2$, CH$_2$—CO—N(C$_2$H$_5$)$_2$, CH(CH$_3$)—CO—N(CH$_3$)$_2$ or CH(CH$_3$)—CO—N(C$_2$H$_5$)$_2$, preferably CH$_2$—CO—N(CH$_3$)$_2$ or CH(CH$_3$)—CO—N(CH$_3$)$_2$;

di(C$_1$–C$_6$-alkyl)aminosulfonyl: for example (CH$_3$)$_2$N—SO$_2$—, (C$_2$H$_5$)$_2$N—SO$_2$—, N,N-dipropylamino-SO$_2$—, N,N-di(1-methylethyl)-amino-SO$_2$—, N,N-dibutylamino-SO$_2$—, N,N-di(1-methylpropyl)-amino-SO$_2$—, N,N-di(2-methylpropyl)amino-SO$_2$—, N,N-di(1,1-dimethylethyl)amino-SO$_2$—, N-ethyl-N-methylamino-SO$_2$—, N-methyl-N-propylamino-SO$_2$—, N-methyl-N-(1-methylethyl)amino-SO$_2$—, N-butyl-N-methylamino-SO$_2$—, N-methyl-N-(1-methylpropyl)amino-SO$_2$—, N-methyl-N-(2-methylpropyl)amino-SO$_2$—, N-(1,1-dimethylethyl)-N-methylamino-SO$_2$—, N-ethyl-N-propylamino-SO$_2$—, N-ethyl-N-(1-methylethyl)amino-SO$_2$—, N-butyl-N-ethylamino-SO$_2$—, N-ethyl-N-(1-methylpropyl)amino-SO$_2$—, N-ethyl-N-(2-methylpropyl)amino-SO$_2$—, N-ethyl-N-(1,1-dimethylethyl)amino-SO$_2$—, N-(1-methylethyl)-N-propylamino-SO$_2$—, N-butyl-N-propylamino-SO$_2$—, N-(1-methylpropyl)-N-propylamino-SO$_2$—, N-(2-methylpropyl)-N-propylamino-SO$_2$—, N-(1,1-dimethylethyl)-N-propylamino-SO$_2$—, N-butyl-N-(1-methylethyl)amino-SO$_2$—, N-(1-methylethyl)-N-(1-methylpropyl)amino-SO$_2$—, N-(1-methylethyl)-N-(2-methylpropyl)amino-SO$_2$—, N-(1,1-dimethylethyl)-N-(1-methylethyl)amino-SO$_2$—, N-butyl-N-(1-methylpropyl)amino-SO$_2$—, N-butyl-N-(2-methylpropyl)amino-SO$_2$—, N-butyl-N-(1,1-dimethylethyl)amino-SO$_2$—, N-(1-methylpropyl)-N-(2-methylpropyl)amino-SO$_2$—, N-(1,1-dimethylethyl)-N-(1-methylpropyl)amino-SO$_2$— or N-(1,1-dimethylethyl)-N-(2-methylpropyl)amino-SO$_2$—, in particular (CH$_3$)$_2$N—SO$_2$—, (C$_2$H$_5$)$_2$N—SO$_2$— or N-ethyl-N-methylamino-SO$_2$—;

C$_3$–C$_6$-alkenyl: for example prop-1-en-1-yl, allyl, 1-methylethenyl, 1-buten-1-yl, 1-buten-2-yl, 1-buten-3-yl, 2-buten-1-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 4-methylpent-4-en-1-yl, 1,1-dimethylbut-2-en-1-yl, 1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

C$_3$–C$_6$-haloalkenyl: C$_3$–C$_6$-alkenyl as mentioned above which is partially or fully substituted by fluorine, chlorine, bromine and/or iodine, ie. for example 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl;

cyano-C$_3$–C$_6$-alkenyl: for example 2-cyanoallyl, 3-cyanoallyl, 4-cyanobut-2-enyl, 4-cyanobut-3-enyl or 5-cyanopent-4-enyl;

C$_3$–C$_6$-alkynyl: prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, preferably prop-2-yn-1-yl;

C$_3$–C$_6$-haloalkynyl: C$_3$–C$_6$-alkynyl as mentioned above which is partially or fully substituted by fluorine, chlorine, bromine and/or iodine, ie. for example 1,1-difluoroprop-2-yn-1-yl, 4-fluorobut-2-yn-1-yl, 4-chlorobut-2-yn-1-yl, 1,1-difluorobut-2-yn-1-yl, 5-fluoropent-3-yn-1-yl or 6-fluorohex-4-yn-1-yl;

cyano-C$_3$–C$_6$-alkynyl: for example 3-cyanopropargyl, 4-cyanobut-2-yn-1-yl, 5-cyanopent-3-yn-1-yl or 6-cyanohex-4-yn-1-yl;

C$_3$–C$_4$-alkenyloxy-C$_1$–C$_4$-alkyl: C$_1$–C$_4$-alkyl which is substituted by C$_3$–C$_4$-alkenyloxy such as allyloxy, but-1-en-3-yloxy, but-1-en-4-yloxy, but-2-en-1-yloxy, 1-methylprop-2-enyloxy or 2-methylprop-2-enyloxy, ie. for example allyloxymethyl, 2-allyloxyethyl or but-1-en-4-yloxymethyl, in particular 2-allyloxyethyl;

C$_3$–C$_4$-alkynyloxy-C$_1$–C$_4$-alkyl: C$_1$–C$_4$-alkyl which is substituted by C$_3$–C$_4$-alkynyloxy such as propargyloxy, but-1-yn-3-yloxy, but-1-yn-4-yloxy, but-2-yn-1-yloxy, 1-methylprop-2-ynyloxy or 2-methylprop-2-ynyloxy, preferably propargyloxy, ie. for example propargyloxymethyl or 2-propargyloxyethyl, in particular 2-propargyloxyethyl;

C$_3$–C$_4$-alkenylthio-C$_1$–C$_4$-alkyl: C$_1$–C$_4$-alkyl which is substituted by C$_3$–C$_4$-alkenylthio such as allylthio, but-1-en-3-ylthio, but-1-en-4-ylthio, but-2-en-1-ylthio, 1-methylprop-2-enylthio or 2-methylprop-2-enylthio, ie. for example allylthiomethyl, 2-allylthioethyl or but-1-en-4-ylthiomethyl, in particular 2-allylthioethyl;

$C_3$–$C_4$-alkynylthio-$C_1$–$C_4$-alkyl: $C_1$–$C_4$-alkyl which is substituted by $C_3$–$C_4$-alkynylthio such as propargylthio, but-1-yn-3-ylthio, but-1-yn-4-ylthio, but-2-yn-1-ylthio, 1-methylprop-2-ynylthio or 2-methylprop-2-ynylthio, preferably propargylthio, ie. for example propargylthiomethyl or 2-propargylthioethyl, in particular 2-propargylthioethyl;

$C_3$–$C_4$-alkenylsulfinyl-$C_1$–$C_4$-alkyl: $C_1$–$C_4$-alkyl which is substituted by $C_3$–$C_4$-alkenylsulfinyl such as allylsulfinyl, but-1-en-3-ylsulfinyl, but-1-en-4-ylsulfinyl, but-2-en-1-ylsulfinyl, 1-methylprop-2-enylsulfinyl or 2-methylprop-2-enylsulfinyl, ie. for example allylsulfinylmethyl, 2-allylsulfinylethyl or but-1-en-4-ylsulfinylmethyl, in particular 2-allylsulfinylethyl;

$C_3$–$C_4$-alkynylsulfinyl-$C_1$–$C_4$-alkyl: $C_1$–$C_4$-alkyl which is substituted by $C_3$–$C_4$-alkynylsulfinyl such as propargylsulfinyl, but-1-yn-3-ylsulfinyl, but-1-yn-4-ylsulfinyl, but-2-yn-1-ylsulfinyl, 1-methylprop-2-ynylsulfinyl or 2-methylprop-2-ynylsulfinyl, preferably propargylsulfinyl, ie. for example propargylsulfinylmethyl or 2-propargylsulfinylethyl, in particular 2-propargylsulfinylethyl;

$C_3$–$C_4$-alkenylsulfonyl-$C_1$–$C_4$-alkyl: $C_1$–$C_4$-alkyl which is substituted by $C_3$–$C_4$-alkenylsulfonyl such as allylsulfonyl, but-1-en-3-ylsulfonyl, but-1-en-4-ylsulfonyl, but-2-en-1-ylsulfonyl, 1-methylprop-2-enylsulfonyl or 2-methylprop-2-enylsulfonyl, ie. for example allylsulfonylmethyl, 2-allylsulfonylethyl or but-1-en-4-ylsulfonylmethyl, in particular 2-allylsulfonylethyl;

$C_3$–$C_4$-alkynylsulfonyl-$C_1$–$C_4$-alkyl: $C_1$–$C_4$-alkyl which is substituted by $C_3$–$C_4$-alkynylsulfonyl such as propargylsulfonyl, but-1-yn-3-ylsulfonyl, but-1-yn-4-ylsulfonyl, but-2-yn-1-ylsulfonyl, 1-methylprop-2-ynylsulfonyl or 2-methylprop-2-ynylsulfonyl, preferably propargylsulfonyl, ie. for example propargylsulfonylmethyl or 2-propargylsulfonylethyl, in particular 2-propargylsulfonylethyl;

$C_3$–$C_8$-cycloalkyl: cyclopropyl, cyclobutyl, cyclopentyl, cyclohexyl, cycloheptyl or cyclooctyl;

$C_3$–$C_8$-cycloalkyl-$C_1$–$C_4$-alkyl: for example cyclopropylmethyl, cyclobutylmethyl, cyclopentylmethyl, cyclohexylmethyl, cycloheptylmethyl, cyclooctylmethyl, 2-(cyclopropyl)ethyl, 2-(cyclobutyl)ethyl, 2-(cyclopentyl)ethyl, 2-(cyclohexyl)ethyl, 2-(cycloheptyl)ethyl, 2-(cyclooctyl)ethyl, 3-(cyclopropyl)propyl, 3-(cyclobutyl)propyl, 3-(cyclopentyl)propyl, 3-(cyclohexyl)propyl, 3-(cycloheptyl)propyl, 3-(cyclooctyl)propyl, 4-(cyclopropyl)butyl, 4-(cyclobutyl)butyl, 4-(cyclopentyl)butyl, 4-(cyclohexyl)butyl, 4-(cycloheptyl)butyl or 4-(cyclooctyl)butyl, in particular cyclopropylmethyl, cyclopentylmethyl or cyclohexylmethyl;

$C_3$–$C_8$-cycloalkyl containing a carbonyl or thiocarbonyl ring member: for example cyclobutanon-2-yl, cyclobutanon-3-yl, cyclopentanon-2-yl, cyclopentanon-3-yl, cyclohexanon-2-yl, cyclohexanon-4-yl, cycloheptanon-2-yl, cyclooctanon-2-yl, cyclobutanethion-2-yl, cyclobutanethion-3-yl, cyclopentanethion-2-yl, cyclopentanethion-3-yl, cyclohexanethion-2-yl, cyclohexanethion-4-yl, cycloheptanethion-2-yl or cyclooctanethion-2-yl, preferably cyclopentanon-2-yl or cyclohexanon-2-yl;

$C_3$–$C_8$-cycloalkyl-$C_1$–$C_4$-alkyl containing a carbonyl or thiocarbonyl ring member: for example cyclobutanon-2-ylmethyl, cyclobutanon-3-ylmethyl, cyclopentanon-2-ylmethyl, cyclopentanon-3-ylmethyl, cyclohexanon-2-ylmethyl, cyclohexanon-4-ylmethyl, cycloheptanon-2-ylmethyl, cyclooctanon-2-ylmethyl, cyclobutanethion-2-ylmethyl, cyclobutanethion-3-ylmethyl, cyclopentanethion-2-ylmethyl, cyclopentanethion-3-ylmethyl, cyclohexanethion-2-ylmethyl, cyclohexanethion-4-ylmethyl, cycloheptanethion-2-ylmethyl, cyclooctanethion-2-ylmethyl, 1-(cyclobutanon-2-yl)ethyl, 1-(cyclobutanon-3-yl)ethyl, 1-(cyclopentanon-2-yl)ethyl, 1-(cyclopentanon-3-yl)ethyl, 1-(cyclohexanon-2-yl)ethyl, 1-(cyclohexanon-4-yl)ethyl, 1-(cycloheptanon-2-yl)ethyl, 1-(cyclooctanon-2-yl)ethyl, 1-(cyclobutanethion-2-yl)ethyl, 1-(cyclobutanethion-3-yl)ethyl, 1-(cyclopentanethion-2-yl)ethyl, 1-(cyclopentanethion-3-yl)ethyl, 1-(cyclohexanethion-2-yl)ethyl, 1-(cyclohexanethion-4-yl)ethyl, 1-(cycloheptanethion-2-yl)ethyl, 1-(cyclooctanethion-2-yl)ethyl, 2-(cyclobutanon-2-yl)ethyl, 2-(cyclobutanon-3-yl)ethyl, 2-(cyclopentanon-2-yl)ethyl, 2-(cyclopentanon-3-yl)ethyl, 2-(cyclohexanon-2-yl)ethyl, 2-(cyclohexanon-4-yl)ethyl, 2-(cycloheptanon-2-yl)ethyl, 2-(cyclooctanon-2-yl)ethyl, 2-(cyclobutanethion-2-yl)ethyl, 2-(cyclobutanethion-3-yl)ethyl, 2-(cyclopentanethion-2-yl)ethyl, 2-(cyclopentanethion-3-yl)ethyl, 2-(cyclohexanethion-2-yl)ethyl, 2-(cyclohexanethion-4-yl)ethyl, 2-(cycloheptanethion-2-yl)ethyl, 2-(cyclooctanethion-2-yl)ethyl, 3-(cyclobutanon-2-yl)propyl, 3-(cyclobutanon-3-yl)propyl, 3-(cyclopentanon-2-yl)propyl, 3-(cyclopentanon-3-yl)propyl, 3-(cyclohexanon-2-yl)propyl, 3-(cyclohexanon-4-yl)propyl, 3-(cycloheptanon-2-yl)propyl, 3-(cyclooctanon-2-yl)propyl, 3-(cyclobutanethion-2-yl)propyl, 3-(cyclobutanethion-3-yl)propyl, 3-(cyclopentanethion-2-yl)propyl, 3-(cyclopentanethion-3-yl)propyl, 3-(cyclohexanethion-2-yl)propyl, 3-(cyclohexanethion-4-yl)propyl, 3-(cycloheptanethion-2-yl)propyl, 3-(cyclooctanethion-2-yl)propyl, 4-(cyclobutanon-2-yl)butyl, 4-(cyclobutanon-3-yl)butyl, 4-(cyclopentanon-2-yl)butyl, 4-(cyclopentanon-3-yl)butyl, 4-(cyclohexanon-2-yl)butyl, 4-(cyclohexanon-4-yl)butyl, 4-(cycloheptanon-2-yl)butyl, 4-(cyclooctanon-2-yl)butyl, 4-(cyclobutanethion-2-yl)butyl, 4-(cyclobutanethion-3-yl)butyl, 4-(cyclopentanethion-2-yl)butyl, 4-(cyclopentanethion-3-yl)butyl, 4-(cyclohexanethion-2-yl)butyl, 4-(cyclohexanethion-4-yl)butyl, 4-(cycloheptanethion-2-yl)butyl or 4-(cyclooctanethion-2-yl)butyl;

$C_3$–$C_8$-cycloalkyloxy-$C_1$–$C_4$-alkyl: cyclopropyloxymethyl, 1-cyclopropyloxyethyl, 2-cyclopropyloxyethyl, 1-cyclopropyloxyprop-1-yl, 2-cyclopropyloxyprop-1-yl, 3-cyclopropyloxyprop-1-yl, 1-cyclopropyloxybut-1-yl, 2-cyclopropyloxybut-1-yl, 3-cyclopropyloxybut-1-yl, 4-cyclopropyloxybut-1-yl, 1-cyclopropyloxybut-2-yl, 2-cyclopropyloxybut-2-yl, 3-cyclopropyloxybut-2-yl, 3-cyclopropyloxybut-2-yl, 4-cyclopropyloxybut-2-yl, 1-(cyclopropyloxymethyl)eth-1-yl,
1-(cyclopropyloxymethyl)-1-(CH$_3$)eth-1-.yl,
1-(cyclopropylmethyloxy)prop-1-yl,
cyclobutyloxymethyl, 1-cyclobutyloxyethyl,
2-cyclobutyloxyethyl, 1-cyclobutyloxyprop-1-yl,
2-cyclobutyloxyprop-1-yl, 3-cyclobutyloxyprop-1-yl,
1-cyclobutyloxybut-1-yl, 2-cyclobutyloxybut-1-yl,
3-cyclobutyloxybut-1-yl, 4-cyclobutyloxybut-1-yl,
1-cyclobutyloxybut-2-yl, 2-cyclobutyloxybut-2-yl,
3-cyclobutyloxybut-2-yl, 3-cyclobutyloxybut-2-yl,
4-cyclobutyloxybut-2-yl, 1-(cyclobutyloxymethyl)eth-1-yl, 1-(cyclobutyloxymethyl)-1-(CH$_3$)eth-1-yl,
1-(cyclobutyloxymethyl)prop-1-yl,
cyclopentyloxymethyl, 1-cyclopentyloxyethyl,
2-cyclopentyloxyethyl, 1-cyclopentyloxyprop-1-yl,
2-cyclopentyloxyprop-1-yl, 3-cyclopentyloxyprop-1-yl, 1-cyclopentyloxybut-1-yl, 2-cyclopentyloxybut-1-yl, 3-cyclopentyloxybut-1-yl, 4-cyclopentyloxybut-1-yl, 1-cyclopentyloxybut-2-yl, 2-cyclopentyloxybut-2-yl, 3-cyclopentyloxybut-2-yl, 3-cyclopentyloxybut-2-yl, 4-cyclopentyloxybut-2-yl,
1-(cyclopentyloxymethyl)eth-1-yl,
1-(cyclopentyloxymethyl)-1-(CH$_3$)eth-1-yl,
1-(cyclopentyloxymethyl)prop-1-yl,
cyclohexyloxymethyl, 1-cyclohexyloxyethyl,
2-cyclohexyloxyethyl, 1-cyclohexyloxyprop-1-yl,
2-cyclohexyloxyprop-1-yl, 3-cyclohexyloxyprop-1-yl,
1-cyclohexyloxybut-1-yl, 2-cyclohexyloxybut-1-yl,
3-cyclohexyloxybut-1-yl, 4-cyclohexyloxybut-1-yl,
1-cyclohexyloxybut-2-yl, 2-cyclohexyloxybut-2-yl,
3-cyclohexyloxybut-2-yl, 3-cyclohexyloxybut-2-yl,
4-cyclohexyloxybut-2-yl, 1-(cyclohexyloxymethyl)eth-1-yl, 1-(cyclohexyloxymethyl)-1-(CH$_3$)eth-1-yl,
1-(cyclohexyloxymethyl)prop-1-yl,
cycloheptyloxymethyl, 1-cycloheptyloxyethyl,
2-cycloheptyloxyethyl, 1-cycloheptyloxyprop-1-yl,
2-cycloheptyloxyprop-1-yl, 3-cycloheptyloxyprop-1-yl, 1-cycloheptyloxybut-1-yl, 2-cycloheptyloxybut-1-yl, 3-cycloheptyloxybut-1-yl, 4-cycloheptyloxybut-1-yl, 1-cycloheptyloxybut-2-yl, 2-cycloheptyloxybut-2-yl, 3-cycloheptyloxybut-2-yl, 3-cycloheptyloxybut-2-yl, 4-cycloheptyloxybut-2-yl,
1-(cycloheptyloxymethyl)eth-1-yl,
1-(cycloheptyloxymethyl)-1-(CH$_3$)eth-1-yl,
1-(cycloheptyloxymethyl)prop-1-yl,
cyclooctyloxymethyl, 1-cyclooctyloxyethyl,
2-cyclooctyloxyethyl, 1-cyclooctyloxyprop-1-yl,
2-cyclooctyloxyprop-1-yl, 3-cyclooctyloxyprop-1-yl,
1-cyclooctyloxybut-1-yl, 2-cyclooctyloxybut-1-yl,
3-cyclooctyloxybut-1-yl, 4-cyclooctyloxybut-1-yl,
1-cyclooctyloxybut-2-yl, 2-cyclooctyloxybut-2-yl,
3-cyclooctyloxybut-2-yl, 3-cyclooctyloxybut-2-yl,
4-cyclooctyloxybut-2-yl, 1-(cyclooctyloxymethyl)eth-1-yl, 1-(cyclooctyloxymethyl)-1-(CH$_3$)eth-1-yl or
1-(cyclooctyloxymethyl)prop-1-yl, in particular
$C_3$–$C_6$-cycloalkoxymethyl or 2-($C_3$–$C_6$-cycloalkoxy) ethyl.

3- to 7-membered heterocyclyl is a saturated, partially or fully unsaturated or aromatic heterocycle having one to three hetero atoms selected from a group consisting of
  one to three nitrogen atoms,
  one or two oxygen and
  one or two sulfur atoms.

Examples of saturated heterocycles which can contain a carbonyl or thiocarbonyl ring member are: oxiranyl, thiiranyl, aziridin-1-yl, aziridin-2-yl, diaziridin-1-yl, diaziridin-3-yl, oxetan-2-yl, oxetan-3-yl, thietan-2-yl, thietan-3-yl, azetidin-1-yl, azetidin-2-yl, azetidin-3-yl, tetrahydrofuran-2-yl, tetrahydrofuran-3-yl, tetrahydrothiophen-2-yl, tetrahydrothiophen-3-yl, pyrrolidin-1-yl, pyrrolidin-2-yl, pyrrolidin-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-oxazolidin-2-yl, 1,3-oxazolidin-3-yl, 1,3-oxazolidin-4-yl, 1,3-oxazolidin-5-yl, 1,2-oxazolidin-2-yl, 1,2-oxazolidin-3-yl, 1,2-oxazolidin-4-yl, 1,2-oxazolidin-5-yl, 1,3-dithiolan-2-yl, 1,3-dithiolan-4-yl, pyrrolidin-1-yl, pyrrolidin-2-yl, pyrrolidin-5-yl, tetrahydropyrazol-1-yl, tetrahydropyrazol-3-yl, tetrahydropyrazol-4-yl, tetrahydropyran-2-yl, tetrahydropyran-3-yl, tetrahydropyran-4-yl, tetrahydrothiopyran-2-yl, tetrahydrothiopyran-3-yl, tetrahydropyran-4-yl, piperidin-1-yl, piperidin-2-yl, piperidin-3-yl, piperidin-4-yl, 1,3-dioxan-2-yl, 1,3-dioxan-4-yl, 1,3-dioxan-5-yl, 1,4-dioxan-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, morpholin-2-yl, morpholin-3-yl, morpholin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, piperazin-3-yl, hexahydro-1,3,5-triazin-1-yl, hexahydro-1,3,5-triazin-2-yl, oxepan-2-yl, oxepan-3-yl, oxepan-4-yl, thiepan-2-yl, thiepan-3-yl, thiepan-4-yl, 1,3-dioxepan-2-yl, 1,3-dioxepan-4-yl, 1,3-dioxepan-5-yl, 1,3-dioxepan-6-yl, 1,3-dithiepan-2-yl, 1,3-dithiepan-2-yl, 1,3-dithiepan-2-yl, 1,3-dithiepan-2-yl, 1,4-dioxepan-2-yl, 1,4-dioxepan-7-yl, hexahydroazepin-1-yl, hexahydroazepin-2-yl, hexahydroazepin-3-yl, hexahydroazepin-4-yl, hexahydro-1,3-diazepin-1-yl, hexahydro-1,3-diazepin-2-yl, hexahydro-1,3-diazepin-4-yl, hexahydro-1,4-diazepin-1-yl and hexahydro-1,4-diazepin-2-yl.

Examples of unsaturated heterocycles which can contain a carbonyl or thiocarbonyl ring member are: dihydrofuran-2-yl, 1,2-oxazolin-3-yl, 1,2-oxazolin-5-yl, 1,3-oxazolin-2-yl.

Preferred heteroaromatics are the 5- and 6-membered heteroaromatics, ie. for example:

furyl, such as 2-furyl and 3-furyl, thienyl, such as 2-thienyl and 3-thienyl, pyrrolyl, such as 2-pyrrolyl and 3-pyrrolyl, isoxazolyl, such as 3-isoxazolyl, 4-isoxazolyl and 5-isoxazolyl, isothiazolyl such as 3-isothiazolyl, 4-isothiazolyl and 5-isothiazolyl, pyrazolyl, such as 3-pyrazolyl, 4-pyrazolyl and 5-pyrazolyl, oxazolyl, such as 2-oxazolyl, 4-oxazolyl and 5-oxazolyl, thiazolyl such as 2-thiazolyl, 4-thiazolyl and 5-thiazolyl, imidazolyl, such as 2-imidazolyl and 4-imidazolyl, oxadiazolyl, such as 1,2,4-oxadiazol-3-yl, 1,2,4-oxadiazol-5-yl and 1,3,4-oxadiazol-2-yl, thiadiazolyl, such as 1,2,4-thiadiazol-3-yl, 1,2,4-thiadiazol-5-yl and 1,3,4-thiadiazol-2-yl, triazolyl, such as 1,2,4-triazol-1-yl, 1,2,4-triazol-3-yl and 1,2,4-triazol-4-yl, pyridinyl, such as 2-pyridinyl, 3-pyridinyl and 4-pyridinyl, pyridazinyl, such as 3-pyridazinyl and 4-pyridazinyl, pyrimidinyl, such as 2-pyrimidinyl, 4-pyrimidinyl and 5-pyrimidinyl, and furthermore 2-pyrazinyl, 1,3,5-triazin-2-yl and 1,2,4-triazin-3-yl, in particular pyridyl, pyrimidyl, furanyl and thienyl.

Preferred with a view to the use of the substituted 2-(benzaryl)pyridines I as herbicides or desiccants/defoliants are those compounds I where the variables have the following meanings, in each case either on their own or in combination:

$R^1$ is $C_1$–$C_4$-haloalkyl or $C_1$–$C_4$-alkylsulfonyl, in particular trifluoromethyl or methylsulfonyl, particularly preferably trifluoromethyl;

$R^2$ is halogen, in particular chlorine;

$R^3$ is hydrogen, fluorine or chlorine, in particular fluorine or chlorine, particularly preferably fluorine;

$R^4$ is cyano or halogen, in particular cyano or chlorine, particularly preferably chlorine;

X is —S—C(ZR$^5$)=N—, the nitrogen being attached to β, —O—C(ZR$^5$)=N—, it being possible for the nitrogen to be attached to α or β, or —N(R$^6$)—C(ZR$^5$)=N—.

The phenyl, carbocyclic and heterocyclic rings mentioned as meanings of $R^5$, $R^6$ and $R^7$ are preferably unsubstituted or carry one substituent.

Very particular preference is given to the substituted 2-(benzaryl)pyridines Ia {≙ where $R^1$=trifluoromethyl, $R^2$ and $R^4$=chlorine, $R^3$=hydrogen, X=—S—C(ZR$^5$)=N— whose nitrogen is attached to position β}, in particular the compounds Ia.001 to Ia.313 listed in Table 1 below:

TABLE 1

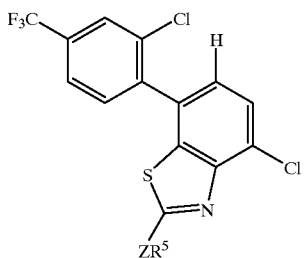

Ia

| No. | —ZR5 |
|---|---|
| Ia.001 | —H |
| Ia.002 | —CH$_3$ |
| Ia.003 | —C$_2$H$_5$ |
| Ia.004 | —(n-C$_3$H$_7$) |
| Ia.005 | —CH(CH$_3$)$_2$ |
| Ia.006 | —(n-C$_4$H$_9$) |
| Ia.007 | —CH$_2$—CH(CH$_3$)$_2$ |
| Ia.008 | —CH(CH$_3$)—C$_2$H$_5$ |
| Ia.009 | —C(CH$_3$)$_3$ |
| Ia.010 | —CH$_2$—CH=CH$_2$ |
| Ia.011 | —CH$_2$—CH=CH—CH$_3$ |
| Ia.012 | —CH$_2$—CH$_2$—CH=CH$_2$ |
| Ia.013 | —CH$_2$—C≡CH |
| Ia.014 | —CH$_2$—OCH$_3$ |
| Ia.015 | —CH$_2$—CH$_2$—OCH$_3$ |
| Ia.016 | —CH$_2$—Cl |
| Ia.017 | —CH$_2$—CN |
| Ia.018 | —CH$_2$—CH$_2$F |
| Ia.019 | —CH$_2$—CF$_3$ |
| Ia.020 | —CH$_2$—CH$_2$Cl |
| Ia.021 | —CH$_2$—CO—OCH$_3$ |
| Ia.022 | —CH$_2$—CO—OC$_2$H$_5$ |
| Ia.023 | —CH$_2$—CO—N(CH$_3$)$_2$ |
| Ia.024 | —CH$_2$—CH(=N—OCH$_3$) |
| Ia.025 | —CH$_2$—CH(=N—OC$_2$H$_5$) |
| Ia.026 | —CH$_2$—CH[=N—O(n-C$_3$H$_7$)] |
| Ia.027 | —CH$_2$—CH[=N—OCH(CH$_3$)$_2$] |
| Ia.028 | —CH$_2$—CH[=N—O(n-C$_4$H$_9$)] |
| Ia.029 | —CH$_2$—CH(=N—OCH$_2$—CH=CH$_2$) |
| Ia.030 | -cyclobutyl |
| Ia.031 | -cyclopentyl |
| Ia.032 | -cyclohexyl |
| Ia.033 | -phenyl |
| Ia.034 | —CH$_2$-cyclobutyl |
| Ia.035 | —CH$_2$-cyclopentyl |
| Ia.036 | —CH$_2$-cyclohexyl |
| Ia.037 | —CH$_2$-phenyl |
| Ia.038 | —NO$_2$ |
| Ia.039 | —CN |
| Ia.040 | —F |
| Ia.041 | —Cl |

TABLE 1-continued

| No. | —ZR5 |
|---|---|
| Ia.042 | —Br |
| Ia.043 | —OCH$_3$ |
| Ia.044 | —OC$_2$H$_5$ |
| Ia.045 | —O(n-C$_3$H$_7$) |
| Ia.046 | —OCH(CH$_3$)$_2$ |
| Ia.047 | —O(n-C$_4$H$_9$) |
| Ia.048 | —OCH$_2$—CH(CH$_3$)$_2$ |
| Ia.049 | —OCH(CH$_3$)—C$_2$H$_5$ |
| Ia.050 | —OC(CH$_3$)$_3$ |
| Ia.051 | —OCH$_2$—CH=CH$_2$ |
| Ia.052 | —OCH$_2$—CH=CH—CH$_3$ |
| Ia.053 | —OCH$_2$—CH$_2$—CH=CH$_2$ |
| Ia.054 | —OCH(CH$_3$)—CH=CH$_2$ |
| Ia.055 | —OCH$_2$—C≡CH |
| Ia.056 | —OCH(CH$_3$)—C≡CH |
| Ia.057 | —OCH$_2$—OCH$_3$ |
| Ia.058 | —OCH$_2$—CH$_2$—OCH$_3$ |
| Ia.059 | —OCH$_2$—CN |
| Ia.060 | —OCH$_2$—CH$_2$F |
| Ia.061 | —OCH$_2$—CF$_3$ |
| Ia.062 | —OCH$_2$—CO—OCH$_3$ |
| Ia.063 | —OCH$_2$—CO—OC$_2$H$_5$ |
| Ia.064 | —OCH$_2$—CO—N(CH$_3$)$_2$ |
| Ia.065 | —OCH$_2$—CH(=N—OCH$_3$) |
| Ia.066 | —OCH$_2$—CH(=N—OC$_2$H$_5$) |
| Ia.067 | —OCH$_2$—CH[=N—O(n-C$_3$H$_7$)] |
| Ia.068 | —OCH$_2$—CH[=N—OCH(CH$_3$)$_2$] |
| Ia.069 | —OCH$_2$—CH[=N—O(n-C$_4$H$_9$)] |
| Ia.070 | —OCH$_2$—CH(=N—OCH$_2$—CH=CH$_2$) |
| Ia.071 | —O-cyclobutyl |
| Ia.072 | —O-cyclopentyl |
| Ia.073 | —O-cyclohexyl |
| Ia.074 | —O-phenyl |
| Ia.075 | —OCH$_2$-cyclobutyl |
| Ia.076 | —OCH$_2$-cyclopentyl |
| Ia.077 | —OCH$_2$-cyclohexyl |
| Ia.078 | —OCH$_2$-phenyl |
| Ia.079 | —CH$_2$—OH |
| Ia.080 | —CH$_2$—OCH$_3$ |
| Ia.081 | —NH$_2$ |
| Ia.082 | —NH—CH$_3$ |
| Ia.083 | —N(CH$_3$)$_2$ |
| Ia.084 | —NH—C$_2$H$_5$ |
| Ia.085 | —N(C$_2$H$_5$)$_2$ |
| Ia.086 | —NH—(n-C$_3$H$_7$) |
| Ia.087 | —N(n-C$_3$H$_7$)$_2$ |
| Ia.088 | —NH—(n-C$_4$H$_9$) |
| Ia.089 | —N(n-C$_4$H$_9$)$_2$ |
| Ia.090 | —NH—CH(CH$_3$)$_2$ |
| Ia.091 | —N[CH(CH$_3$)$_2$]$_2$ |
| Ia.092 | —NH—CH$_2$—CH(CH$_3$)$_2$ |
| Ia.093 | —N[CH$_2$—CH(CH$_3$)$_2$]$_2$ |
| Ia.094 | —NH—CH$_2$—CH=CH$_2$ |
| Ia.095 | —N(CH$_2$—CH=CH$_2$)$_2$ |
| Ia.096 | —NH—CH$_2$—C≡CH |
| Ia.097 | —N(CH$_2$—C≡CH)$_2$ |
| Ia.098 | —CH$_2$—N(CH$_3$)$_2$ |
| Ia.099 | —SH |
| Ia.100 | —SCH$_3$ |
| Ia.101 | —SC$_2$H$_5$ |
| Ia.102 | —S(n-C$_3$H$_7$) |
| Ia.103 | —S(n-C$_4$H$_9$) |

TABLE 1-continued

Ia

| No. | —ZR5 |
|---|---|
| Ia.104 | —SCH(CH$_3$)$_2$ |
| Ia.105 | —SCH$_2$—CH(CH$_3$)$_2$ |
| Ia.106 | —SCH(CH$_3$)—C$_2$H$_5$ |
| Ia.107 | —SC(CH$_3$)$_3$ |
| Ia.108 | —SCH$_2$—CH=CH$_2$ |
| Ia.109 | —SCH$_2$—CH=CH—CH$_3$ |
| Ia.110 | —SCH$_2$—CH$_2$—CH=CH$_2$ |
| Ia.111 | —SCH(CH$_3$)—CH=CH$_2$ |
| Ia.112 | —SCH$_2$—C≡CH |
| Ia.113 | —SCH(CH$_3$)—C≡CH |
| Ia.114 | —SCH$_2$—OCH$_3$ |
| Ia.115 | —SCH$_2$—CH$_2$—OCH$_3$ |
| Ia.116 | —SCH$_2$—CN |
| Ia.117 | —SCH$_2$—CH$_2$F |
| Ia.118 | —SCH$_2$—CF$_3$ |
| Ia.119 | —SCH$_2$—CH$_2$Cl |
| Ia.120 | —SCH$_2$—CO—OCH$_3$ |
| Ia.121 | —SCH$_2$—CO—OC$_2$H$_5$ |
| Ia.122 | —SCH$_2$—CO—N(CH$_3$)$_2$ |
| Ia.123 | —SCH$_2$—CH(=N—OCH$_3$) |
| Ia.124 | —SCH$_2$—CH(=N—OC$_2$H$_5$) |
| Ia.125 | —SCH$_2$—CH[=N—O(n-C$_3$H$_7$)] |
| Ia.126 | —SCH$_2$—CH[=N—OCH(CH$_3$)$_2$] |
| Ia.127 | —SCH$_2$—CH[=N—O(n-C$_4$H$_9$)] |
| Ia.128 | —SCH$_2$—CH(=N—OCH$_2$—CH=CH$_2$) |
| Ia.129 | —S-cyclobutyl |
| Ia.130 | —S-cyclopentyl |
| Ia.131 | —S-cyclohexyl |
| Ia.132 | —S-phenyl |
| Ia.133 | —SCH$_2$-cyclobutyl |
| Ia.134 | —SCH$_2$-cyclopentyl |
| Ia.135 | —SCH$_2$-cyclohexyl |
| Ia.136 | —SCH$_2$-phenyl |
| Ia.137 | —CH$_2$—SCH$_3$ |
| Ia.138 | —SO—CH$_3$ |
| Ia.139 | —SO—C$_2$H$_5$ |
| Ia.140 | —SO—(n-C$_3$H$_7$) |
| Ia.141 | —SO—(n-C$_4$H$_9$) |
| Ia.142 | —SO—CH(CH$_3$)$_2$ |
| Ia.143 | —SO—CH$_2$—CH(CH$_3$)$_2$ |
| Ia.144 | —SO—CH(CH$_3$)—C$_2$H$_5$ |
| Ia.145 | —SO—C(CH$_3$)$_3$ |
| Ia.146 | —SO—CH$_2$—CH=CH$_2$ |
| Ia.147 | —SO—CH$_2$—CH=CH—CH$_3$ |
| Ia.148 | —SO—CH$_2$—CH$_2$—CH=CH$_2$ |
| Ia.149 | —SO—CH(CH$_3$)—CH=CH$_2$ |
| Ia.150 | —SO—CH$_2$—C≡CH |
| Ia.151 | —SO—CH(CH$_3$)—C≡CH |
| Ia.152 | —SO—CH$_2$—OCH$_3$ |
| Ia.153 | —SO—CH$_2$—CH$_2$—OCH$_3$ |
| Ia.154 | —SO—CH$_2$—CN |
| Ia.155 | —SO—CH$_2$—CH$_2$F |
| Ia.156 | —SO—CH$_2$—CF$_3$ |
| Ia.157 | —SO—CH$_2$—CH$_2$Cl |
| Ia.158 | —SO—CH$_2$—CO—OCH$_3$ |
| Ia.159 | —SO—CH$_2$—CO—OC$_2$H$_5$ |
| Ia.160 | —SO—CH$_2$—CO—N(CH$_3$)$_2$ |
| Ia.161 | —SO—CH$_2$—CH(=N—OCH$_3$) |
| Ia.162 | —SO—CH$_2$—CH(=N—OC$_2$H$_5$) |
| Ia.163 | —SO—CH$_2$—CH[=N—O(n-C$_3$H$_7$)] |
| Ia.164 | —SO—CH$_2$—CH[=N—OCH(CH$_3$)$_2$] |
| Ia.165 | —SO—CH$_2$—CH[=N—O(n-C$_4$H$_9$)] |
| Ia.166 | —SO—CH$_2$—CH(=N—OCH$_2$—CH=CH$_2$) |
| Ia.167 | —SO-cyclobutyl |
| Ia.168 | —SO-cyclopentyl |
| Ia.169 | —SO-cyclohexyl |
| Ia.170 | —SO-phenyl |
| Ia.171 | —SO—CH$_2$-cyclobutyl |
| Ia.172 | —SO—CH$_2$-cyclopentyl |
| Ia.173 | —SO—CH$_2$-cyclohexyl |
| Ia.174 | —SO—CH$_2$-phenyl |
| Ia.175 | —CH$_2$—SO—CH$_3$ |
| Ia.176 | —SO$_2$CH$_3$ |
| Ia.177 | —SO$_2$—C$_2$H$_5$ |
| Ia.178 | —SO$_2$—(n-C$_3$H$_7$) |
| Ia.179 | —SO$_2$—(n-C$_4$H$_9$) |
| Ia.180 | —SO$_2$—CH(CH$_3$)$_2$ |
| Ia.181 | —SO$_2$—CH$_2$—CH(CH$_3$)$_2$ |
| Ia.182 | —SO$_2$—CH(CH$_3$)—C$_2$H$_5$ |
| Ia.183 | —SO$_2$—C(CH$_3$)$_3$ |
| Ia.184 | —SO$_2$—CH$_2$—CH=CH$_2$ |
| Ia.185 | —SO$_2$—CH$_2$—CH=CH—CH$_3$ |
| Ia.186 | —SO$_2$—CH$_2$—CH$_2$—CH=CH$_2$ |
| Ia.187 | —SO$_2$—CH(CH$_3$)—CH=CH$_2$ |
| Ia.188 | —SO$_2$—CH$_2$—C≡CH |
| Ia.189 | —SO$_2$—CH(CH$_3$)—C≡CH |
| Ia.190 | —SO$_2$—CH$_2$—OCH$_3$ |
| Ia.191 | —SO$_2$—CH$_2$—CH$_2$—OCH$_3$ |
| Ia.192 | —SO$_2$—CH$_2$—CN |
| Ia.193 | —SO$_2$—CH$_2$—CH$_2$F |
| Ia.194 | —SO$_2$—CH$_2$—CF$_3$ |
| Ia.195 | —SO$_2$—CH$_2$—CH$_2$Cl |
| Ia.196 | —SO$_2$—CH$_2$—CO—OCH$_3$ |
| Ia.197 | —SO$_2$—CH$_2$—CO—OC$_2$H$_5$ |
| Ia.198 | —SO$_2$—CH$_2$—CO—N(CH$_3$)$_2$ |
| Ia.199 | —SO$_2$—CH$_2$—CH(=N—OCH$_3$) |
| Ia.200 | —SO$_2$—CH$_2$—CH(=N—OC$_2$H$_5$) |
| Ia.201 | —SO$_2$—CH$_2$—CH[=N—O(n-C$_3$H$_7$)] |
| Ia.202 | —SO$_2$—CH$_2$—CH[=N—OCH(CH$_3$)$_2$] |
| Ia.203 | —SO$_2$—CH$_2$—CH[=N—O(n-C$_4$H$_9$)] |
| Ia.204 | —SO$_2$—CH$_2$—CH(=N—OCH$_2$—CH=CH$_2$) |
| Ia.205 | —SO$_2$-cyclobutyl |
| Ia.206 | —SO$_2$-cyclopentyl |
| Ia.207 | —SO$_2$-cyclohexyl |
| Ia.208 | —SO$_2$-phenyl |
| Ia.209 | —SO$_2$—CH$_2$-cyclobutyl |
| Ia.210 | —SO$_2$—CH$_2$-cyclopentyl |
| Ia.211 | —SO$_2$—CH$_2$-cyclohexyl |
| Ia.212 | —SO$_2$—CH$_2$-phenyl |
| Ia.213 | —CH$_2$—SO$_2$—CH$_3$ |
| Ia.214 | —CH$_2$—CH(Cl)—CO—OH |
| Ia.215 | —CH$_2$—CH(Cl)—CO—OCH$_3$ |
| Ia.216 | —CH$_2$—CH(Cl)—CO—OC$_2$H$_5$ |
| Ia.217 | —CH$_2$—CH(Cl)—CO—O(n-C$_3$H$_7$) |
| Ia.218 | —CH$_2$—CH(Cl)—CO—O(n-C$_4$H$_9$) |
| Ia.219 | —CH$_2$—CH(Cl)—CO—OCH(CH$_3$)$_2$ |
| Ia.220 | —CH$_2$—CH(Cl)—CO—OCH$_2$—CH(CH$_3$)$_2$ |
| Ia.221 | —CH$_2$—CH(Cl)—CO—OCH(CH$_3$)—C$_2$H$_5$ |
| Ia.222 | —CH$_2$—CH(Cl)—CO—OC(CH$_3$)$_3$ |
| Ia.223 | —CH$_2$—CH(Br)—CO—OH |
| Ia.224 | —CH$_2$—CH(Br)—CO—OCH$_3$ |
| Ia.225 | —CH$_2$—CH(Br)—CO—OC$_2$H$_5$ |
| Ia.226 | —CH$_2$—CH(Br)—CO—O(n-C$_3$H$_7$) |
| Ia.227 | —CH$_2$—CH(Br)—CO—O(n-C$_4$H$_9$) |

TABLE 1-continued

Ia

| No. | —ZR5 |
|---|---|
| Ia.228 | —CH$_2$—CH(Br)—CO—OCH(CH$_3$)$_2$ |
| Ia.229 | —CH$_2$—CH(Br)—CO—OCH$_2$—CH(CH$_3$)$_2$ |
| Ia.230 | —CH$_2$—CH(Br)—CO—OCH(CH$_3$)—C$_2$H$_5$ |
| Ia.231 | —CH$_2$—CH(Br)—CO—OC(CH$_3$)$_3$ |
| Ia.232 | —CH=CH—CO—OH |
| Ia.233 | —CH=CH—CO—OCH$_3$ |
| Ia.234 | —CH=CH—CO—OC$_2$H$_5$ |
| Ia.235 | —CH=CH—CO—O(n-C$_3$H$_7$) |
| Ia.236 | —CH=CH—CO—O(n-C$_4$H$_9$) |
| Ia.237 | —CH=CH—CO—OCH(CH$_3$)$_2$ |
| Ia.238 | —CH=CH—CO—OCH$_2$—CH(CH$_3$)$_2$ |
| Ia.239 | —CH=CH—CO—OCH(CH$_3$)—C$_2$H$_5$ |
| Ia.240 | —CH=CH—CO—OC(CH$_3$)$_3$ |
| Ia.241 | —CH=C(Cl)—CO—OH |
| Ia.242 | —CH=C(Cl)—CO—OCH$_3$ |
| Ia.243 | —CH=C(Cl)—CO—OC$_2$H$_5$ |
| Ia.244 | —CH=C(Cl)—CO—O(n-C$_3$H$_7$) |
| Ia.245 | —CH=C(Cl)—CO—O(n-C$_4$H$_9$) |
| Ia.246 | —CH=C(Cl)—CO—OCH(CH$_3$)$_2$ |
| Ia.247 | —CH=C(Cl)—CO—OCH$_2$—CH(CH$_3$)$_2$ |
| Ia.248 | —CH=C(Cl)—CO—OCH(CH$_3$)—C$_2$H$_5$ |
| Ia.249 | —CH=C(Cl)—CO—OC(CH$_3$)$_3$ |
| Ia.250 | —CH=C(Br)—CO—OH |
| Ia.251 | —CH=C(Br)—CO—OCH$_3$ |
| Ia.252 | —CH=C(Br)—CO—OC$_2$H$_5$ |
| Ia.253 | —CH=C(Br)—CO—O(n-C$_3$H$_7$) |
| Ia.254 | —CH=C(Br)—CO—O(n-C$_4$H$_9$) |
| Ia.255 | —CH=C(Br)—CO—OCH(CH$_3$)$_2$ |
| Ia.256 | —CH=C(Br)—CO—OCH$_2$—CH(CH$_3$)$_2$ |
| Ia.257 | —CH=C(Br)—CO—OCH(CH$_3$)—C$_2$H$_5$ |
| Ia.258 | —CH=C(Br)—CO—OC(CH$_3$)$_3$ |
| Ia.259 | —CH$_2$—CH(Cl)—CO—NH$_2$ |
| Ia.260 | —CH$_2$—CH(Cl)—CO—NH—CH$_3$ |
| Ia.261 | —CH$_2$—CH(Cl)—CO—N(CH$_3$)$_2$ |
| Ia.262 | —CH$_2$—CH(Cl)—CO—NH—C$_2$H$_5$ |
| Ia.263 | —CH$_2$—CH(Cl)—CO—N(C$_2$H$_5$)$_2$ |
| Ia.264 | —CH$_2$—CH(Cl)—CO—NH—(n-C$_3$H$_7$) |
| Ia.265 | —CH$_2$—CH(Cl)—CO—N(n-C$_3$H$_7$)$_2$ |
| Ia.266 | —CH$_2$—CH(Cl)—CO—NH—(n-C$_4$H$_9$) |
| Ia.267 | —CH$_2$—CH(Cl)—CO—N(n-C$_4$H$_9$)$_2$ |
| Ia.268 | —CH$_2$—CH(Br)—CO—NH$_2$ |
| Ia.269 | —CH$_2$—CH(Br)—CO—NH—CH$_3$ |
| Ia.270 | —CH$_2$—CH(Br)—CO—N(CH$_3$)$_2$ |
| Ia.271 | —CH$_2$—CH(Br)—CO—NH—C$_2$H$_5$ |
| Ia.272 | —CH$_2$—CH(Br)—CO—N(C$_2$H$_5$)$_2$ |
| Ia.273 | —CH$_2$—CH(Br)—CO—NH—(n-C$_3$H$_7$) |
| Ia.274 | —CH$_2$—CH(Br)—CO—N(n-C$_3$H$_7$)$_2$ |
| Ia.275 | —CH$_2$—CH(Br)—CO—NH—(n-C$_4$H$_9$) |
| Ia.276 | —CH$_2$—CH(Br)—CO—N(n-C$_4$H$_9$)$_2$ |
| Ia.277 | —CH=CH—CO—NH$_2$ |
| Ia.278 | —CH=CH—CO—NH—CH$_3$ |
| Ia.279 | —CH=CH—CO—N(CH$_3$)$_2$ |
| Ia.280 | —CH=CH—CO—NH—C$_2$H$_5$ |
| Ia.281 | —CH=CH—CO—N(C$_2$H$_5$)$_2$ |
| Ia.282 | —CH=CH—CO—NH—(n-C$_3$H$_7$) |
| Ia.283 | —CH=CH—CO—N(n-C$_3$H$_7$)$_2$ |
| Ia.284 | —CH=CH—CO—NH—(n-C$_4$H$_9$) |
| Ia.285 | —CH=CH—CO—N(n-C$_4$H$_9$)$_2$ |
| Ia.286 | —CH=C(Cl)—CO—NH$_2$ |
| Ia.287 | —CH=C(Cl)—CO—NH—CH$_3$ |
| Ia.288 | —CH=C(Cl)—CO—N(CH$_3$)$_2$ |
| Ia.289 | —CH=C(Cl)—CO—NH—C$_2$H$_5$ |

TABLE 1-continued

Ia

| No. | —ZR5 |
|---|---|
| Ia.290 | —CH=C(Cl)—CO—N(C$_2$H$_5$)$_2$ |
| Ia.291 | —CH=C(Cl)—CO—NH—(n-C$_3$H$_7$) |
| Ia.292 | —CH=C(Cl)—CO—N(n-C$_3$H$_7$)$_2$ |
| Ia.293 | —CH=C(Cl)—CO—NH—(n-C$_4$H$_9$) |
| Ia.294 | —CH=C(Cl)—CO—N(n-C$_4$H$_9$)$_2$ |
| Ia.295 | —CH=C(Br)—CO—NH$_2$ |
| Ia.296 | —CH=C(Br)—CO—NH—CH$_3$ |
| Ia.297 | —CH=C(Br)—CO—NH(CH$_3$)$_2$ |
| Ia.298 | —CH=C(Br)—CO—NH—C$_2$H$_5$ |
| Ia.299 | —CH=C(Br)—CO—N(C$_2$H$_5$)$_2$ |
| Ia.300 | —CH=C(Br)—CO—NH—(n-C$_3$H$_7$) |
| Ia.301 | —CH=C(Br)—CO—N(n-C$_3$H$_7$)$_2$ |
| Ia.302 | —CH=C(Br)—CO—NH—(n-C$_4$H$_9$) |
| Ia.303 | —CH=C(Br)—CO—N(n-C$_4$H$_9$)$_2$ |
| Ia.304 | —NH—SO$_2$—CH$_3$ |
| Ia.305 | —N(SO$_2$—CH$_3$)$_2$ |
| Ia.306 | —NH—SO$_2$—C$_2$H$_5$ |
| Ia.307 | —N(SO$_2$—C$_2$H$_5$)$_2$ |
| Ia.308 | —NH—SO$_2$—CH$_2$—C$_2$H$_5$ |
| Ia.309 | —NH—CHO |
| Ia.310 | —NH—CO—CH$_3$ |
| Ia.311 | —NH—CO—C$_2$H$_5$ |
| Ia.312 | —N(CO—CH$_3$)—SO$_2$—CH$_3$ |
| Ia.313 | —N(CO—CH$_3$)—SO$_2$—C$_2$H$_5$ |

Furthermore, particular preference is given to the substituted 2-(benzaryl)pyridines of the formulae Ib to Iz and Iα to Iδ, in particular to the compounds Ib.001 to Ib.313, which differ from the corresponding compounds Ia.001 to Ia.313 only in that R$^3$ is chlorine:

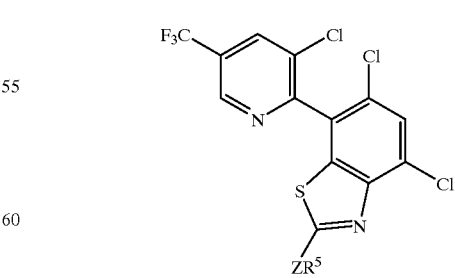

the compounds Ic.001 to Ic.313, which differ from the corresponding compounds Ia.001 to Ia.313 only in that R$^3$ is fluorine:

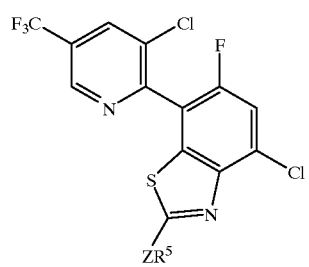

Ic

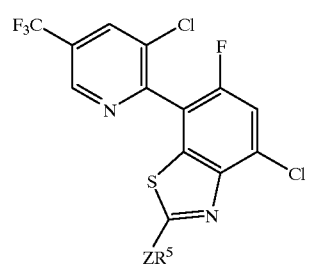

Ig the compounds Id.001 to Id.313, which differ from the corresponding compounds Ia.001 to Ia.313 only in that $R^1$ is methylsulfonyl:

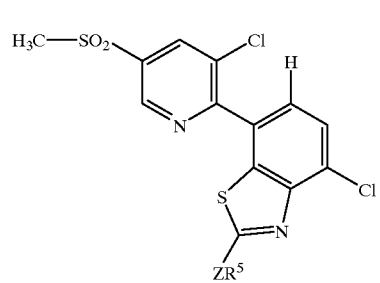

Id the compounds Ih.001 to Ih.313, which differ from the corresponding compounds Ia.001 to Ia.313 only in that X is —O—C(ZR$^5$)=N— whose nitrogen is attached to position α:

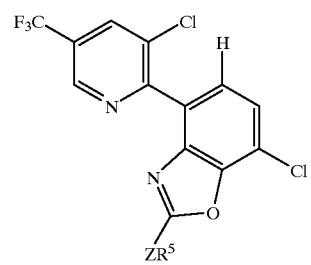

Ih the compounds Ie.001 to Ie.313, which differ from the corresponding compounds Ia.001 to Ia.313 only in that $R^1$ is methylsulfonyl and $R^3$ is fluorine:

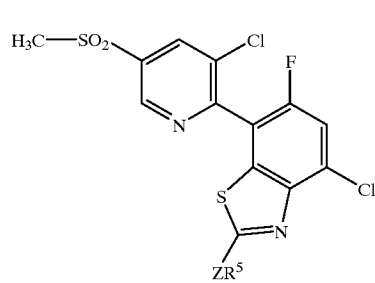

Ie the compounds Ii.001 to Ii.313, which differ from the corresponding compounds Ia.001 to Ia.313 only in that X is —O—C(ZR$^5$)=N— whose nitrogen is attached to position α and $R^3$ is chlorine:

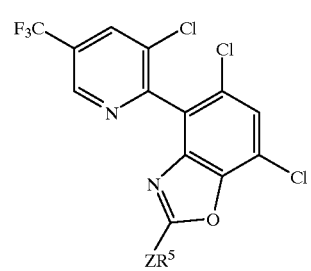

Ii the compounds If.001 to If.313, which differ from the corresponding compounds Ia.001 to Ia.313 only in that $R^4$ is cyano:

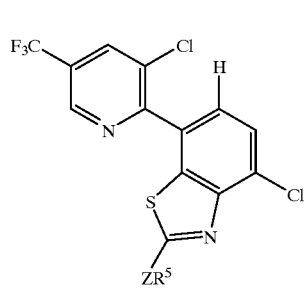

If the compounds Ik.001 to Ik.313, which differ from the corresponding compounds Ia.001 to Ia.313 only in that X is —O—C(ZR$^5$)=N— whose nitrogen is attached to position α and $R^3$ is fluorine:

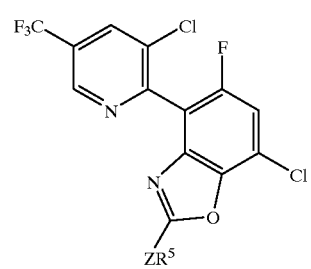

Ik the compounds Ig.001 to Ig.313, which differ from the corresponding compounds Ia.001 to Ia.313 only in that $R^3$ is fluorine and $R^4$ is cyano:

the compounds Im.001 to Im.313, which differ from the corresponding compounds Ia.001 to Ia.313 only in that X is —O—C(ZR⁵)=N— whose nitrogen is attached to position α and R¹ is methylsulfonyl:

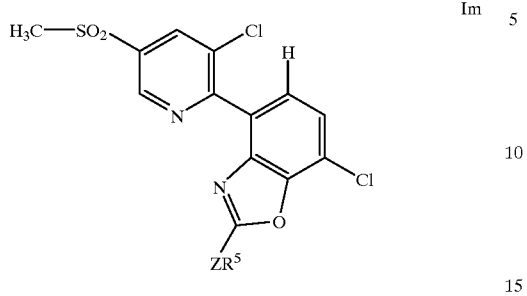
Im the compounds In.001 to In.313, which differ from the corresponding compounds Ia.001 to Ia.313 only in that X is —O—C(ZR⁵)=N— whose nitrogen is attached to position α, R¹ is methylsulfonyl and R³ is fluorine:

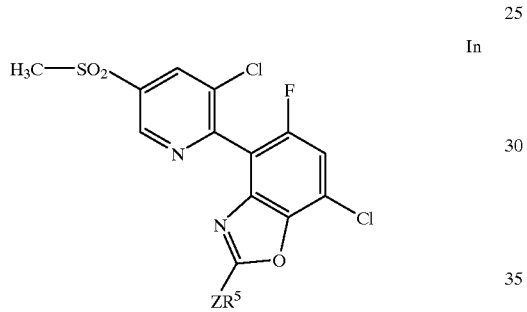
In the compounds Io.001 to Io.313, which differ from the corresponding compounds Ia.001 to Ia.313 only in that X is —O—C(ZR⁵)=N— whose nitrogen is attached to position α and R⁴ is cyano:

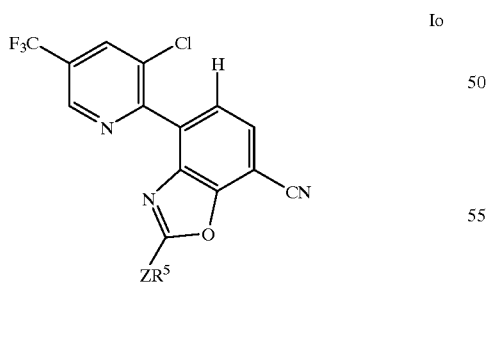
Io the compounds Ip.001 to Ip.313, which differ from the corresponding compounds Ia.001 to Ia.313 only in that X is —O—C(ZR⁵)=N— whose nitrogen is attached to position α, R³ is fluorine and R⁴ is cyano:

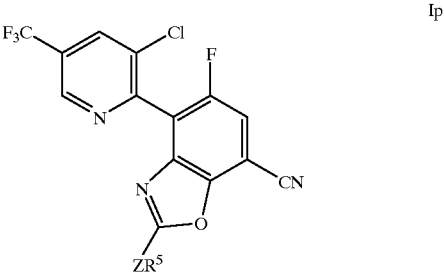
Ip the compounds Iq.001 to Iq.313, which differ from the corresponding compounds Ia.001 to Ia.313 only in that X is —N(CH₃)—C(ZR⁵)=N— whose unsubstituted imino nitrogen is attached to position α:

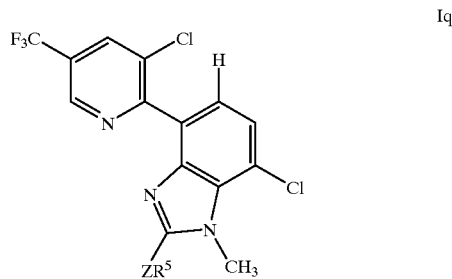
Iq the compounds Ir.001 to Ir.313, which differ from the corresponding compounds Ia.001 to Ia.313 only in that X is —N(CH₃)—C(ZR⁵)=N— whose unsubstituted imino-nitrogen is attached to position α and R³ is chlorine:

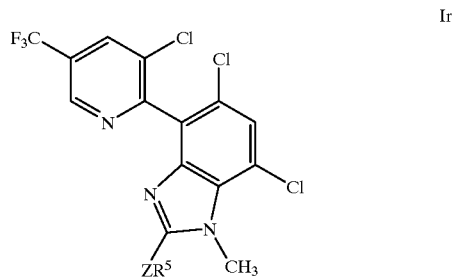
Ir the compounds Is.001 to Is.313, which differ from the corresponding compounds Ia.001 to Ia.313 only in that X is —N(CH₃)—C(ZR⁵)=N— whose unsubstituted imino-nitrogen is attached to position α and R³ is fluorine:

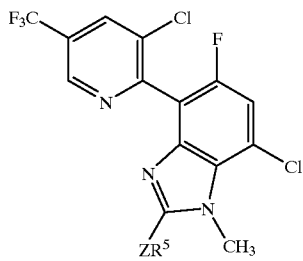

Is

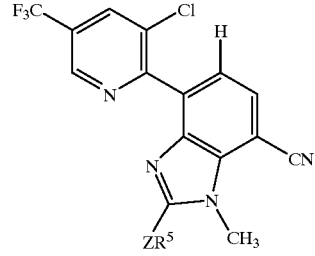

Iv the compounds It.001 to It.313, which differ from the corresponding compounds Ia.001 to Ia.313 only in that X is —N(CH$_3$)—C(ZR$^5$)=N— whose unsubstituted imino-nitrogen is attached to position α and R$^1$ is methylsulfonyl:

the compounds Iw.001 to Iw.313, which differ from the corresponding compounds Ia.001 to Ia.313 only in that X is —N(CH$_3$)—C(ZR$^5$)=N— whose unsubstituted imino-nitrogen is attached to position α, R$^3$ is fluorine and R$^4$ is cyano:

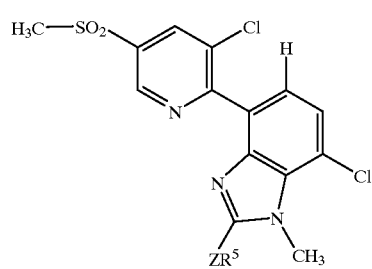

It

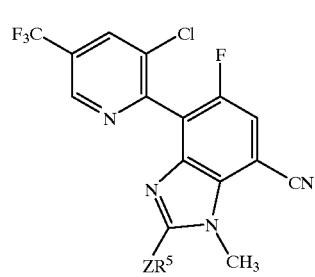

Iw the compounds Iu.001 to Iu.313, which differ from the corresponding compounds Ia.001 to Ia.313 only in that X is —N(CH$_3$)—C(ZR$^5$)=N— whose unsubstituted imino-nitrogen is attached to position α, R$^1$ is methylsulfonyl and R$^3$ is fluorine:

the compounds Ix.001 to Ix.313, which differ from the corresponding compounds Ia.001 to Ia.313 only in that X is —O—C(ZR$^5$)=N— whose nitrogen is attached to position β:

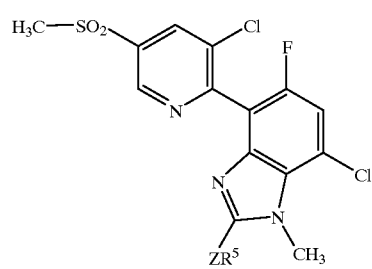

Iu

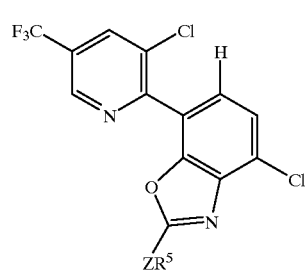

Ix the compounds Iv.001 to Iv.313, which differ from the corresponding compounds Ia.001 to Ia.313 only in that X is —N(CH$_3$)—C(ZR$^5$)=N— whose unsubstituted imino-nitrogen is attached to position α and R$^4$ is cyano:

the compounds Iy.001 to Iy.313, which differ from the corresponding compounds Ia.001 to Ia.313 only in that X is —O—C(ZR$^5$)=N— whose nitrogen is attached to position β and R$^3$ is chlorine:

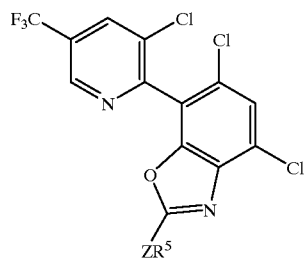

Iy

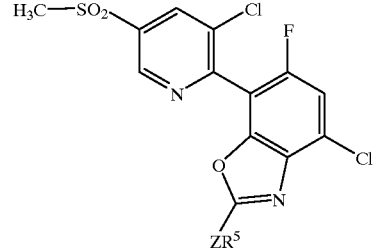

Iβ the compounds Iy.001 to Iy.313, which differ from the corresponding compounds Ia.001 to Ia.313 only in that X is —O—C(ZR$^5$)=N— whose nitrogen is attached to position β and R$^4$ is cyano:

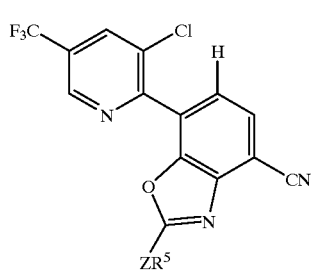

Iγ the compounds Iz.001 to Iz.313, which differ from the corresponding compounds Ia.001 to Ia.313 only in that X is —O—C(ZR$^5$)=N— whose nitrogen is attached to position β and R$^3$ is fluorine:

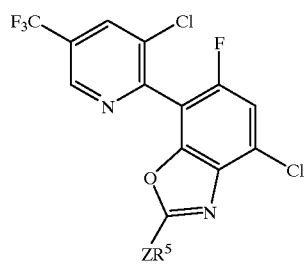

Iz the compounds Iδ.001 to Iδ.313, which differ from the corresponding compounds Ia.001 to Ia.313 only in that X is —O—C(ZR$^5$)=N— whose nitrogen is attached to position β, R$^3$ is fluorine and R$^4$ is cyano:

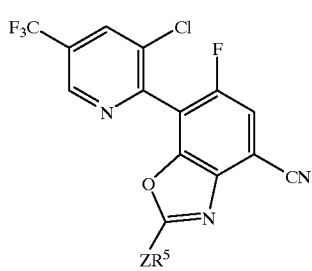

Iδ the compounds Iα.001 to Iα.313, which differ from the corresponding compounds Ia.001 to Ia.313 only in that X is —O—C(ZR$^5$)=N— whose nitrogen is attached to position β and R$^1$ is methylsulfonyl:

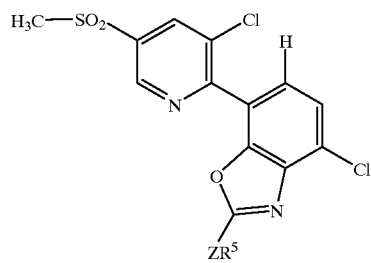

Iα the compounds Iβ.001 to Iβ.313, which differ from the corresponding compounds Ia.001 to Ia.313 only in that X is —O—C(ZR$^5$)=N— whose nitrogen is attached to position β, R$^1$ is methylsulfonyl and R$^3$ is fluorine:

The substituted 2-(benzaryl)pyridines of the formula I can be obtained in a variety of ways, in particular according to one of the following processes:

A) Reaction of a 2-(aminophenyl)pyridine of the formula II with a halogen and ammonium thiocyanate or with an alkali metal thiocyanate or alkaline earth metal thiocyanate:

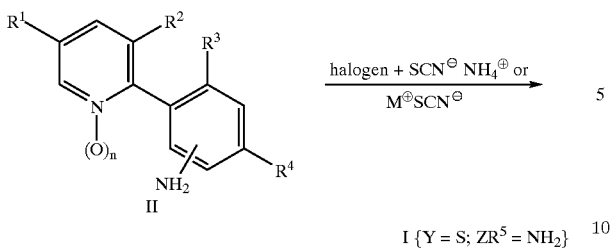

$M^\oplus$ = an alkali metal ion or ½ alkaline earth metal ion.

Preferred halogen is chlorine or bromine; amongst the alkali metal/alkaline earth metal thiocyanates, preference is given to sodium thiocyanate.

In general, the reaction is carried out in an inert solvent/diluent, for example in a hydrocarbon such as toluene and hexane, in a halogenated hydrocarbon such as dichloromethane, in an ether such as tetrahydrofuran, in an alcohol such as ethanol, in a carboxylic acid such as acetic acid, or in an aprotic solvent such as dimethylformamide, acetonitrile and dimethyl sulfoxide.

The reaction is usually carried out between the melting point and the boiling point of the reaction mixture, preferably from 0 to 150° C.

To obtain a very high yield of the product of value, halogen and ammonium thiocyanate or alkali metal/alkaline earth metal thiocyanate are employed in about equimolar amounts or in an excess of up to 5 times the molar amount, based on the amount of II.

The 2-(aminophenyl)pyridines II are obtainable for example by reducing the corresponding 2-(nitrophenyl)pyridines III {cf. for example Organikum, VEB Verlag, Berlin 1986, p.534–536}:

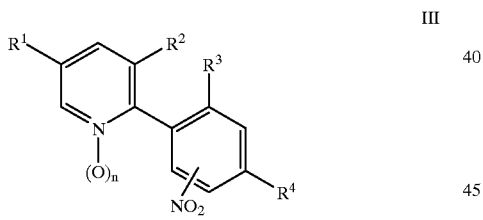

The 2-(nitrophenyl)pyridines III themselves are advantageously preparable by nitration of phenylpyridines IV {cf. for example Organikum, VEB-Verlag, Berlin 1986, p.304–307}:

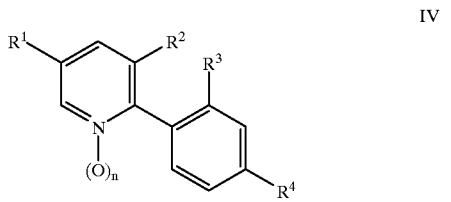

B) Reaction of a 2-(aminohydroxyphenyl)pyridine of the formula Va or Vb with a carboxylic acid derivative or carbonic acid derivative {cf. also H. Döpp & D. Döpp in Houben-Weyl, Methoden der organischen Chemie, Vol. E8a, Thieme Verlag, Stuttgart 1993, p.1020–1170}:

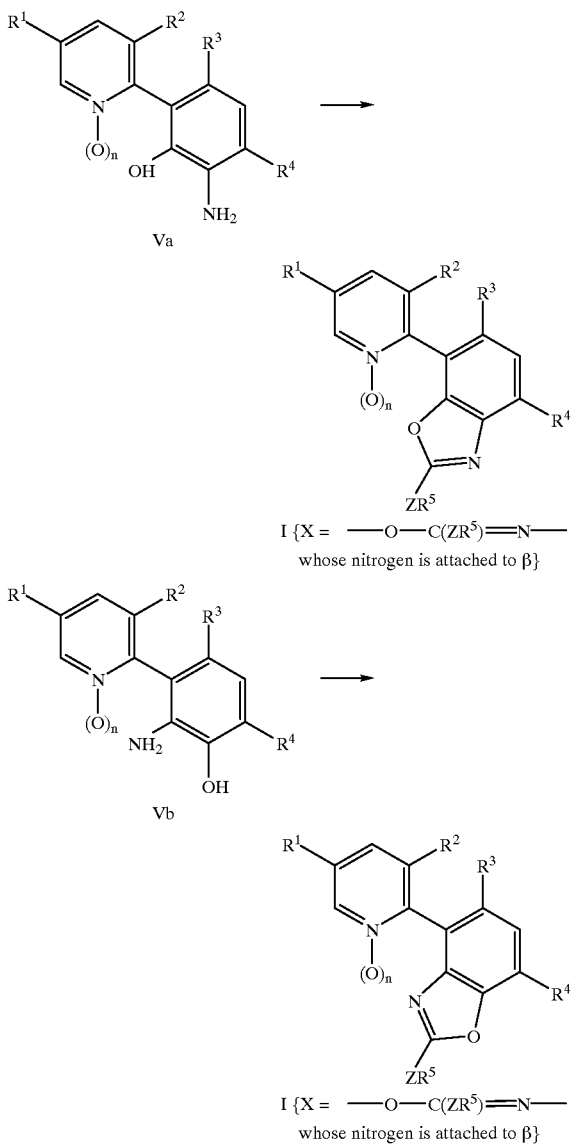

Carboxylic acid derivatives and carbonic acid derivatives are, for example, $COCl_2$, $OC(Cl)$—$OR^9$, $OC(OR^9)_2$, $CS_2$, $K^\oplus S_2C^\ominus$—$OR^9$, $Cl_2C$=$N^\oplus(R^9, R^{10}) Cl^\ominus$, anhydrides and orthoesters such as $R^5$—$(O)_{0,1}$—$C(OR^9)_3$ where $R^9$ and $R^{10}$ are in each case $C_1$–$C_4$-alkyl, in particular methyl, ethyl or n-propyl.

In general, the reaction is carried out in an inert solvent/diluent, for example in a hydrocarbon such as toluene and hexane, in a halogenated hydrocarbon such as dichloromethane, in an ether such as tetrahydrofuran, in an alcohol such as ethanol or in an aprotic solvent such as dimethylformamide or dimethylsulfoxide.

It is recommended to carry out the reaction in the alcohol $R^9OH$.

The reaction is usually carried out between the melting point and the boiling point of the reaction mixture, preferably at from 0 to 150° C.

To obtain a very high yield of the product of value, the orthoester is employed in an about equimolar amount or in an excess of up to 5 times the molar amount, based on the amount of Va or Vb.

The 2-(aminohydroxyphenyl)pyridines Va/Vb are advantageously obtainable by reduction of the corresponding 2-[nitro(hydroxy/alkoxy)phenyl]pyridines VIa/VIb

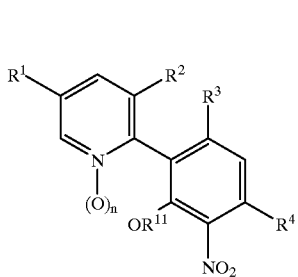

VIa

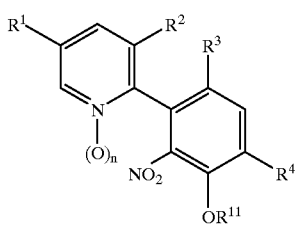

VIb

{for this, cf. for example Organikum, VEB-Verlag, Berlin 1986, p.34–36 and Org. Synth. Coll. Vol. 3 (1943), 471}, which in turn can be prepared by nitration of the corresponding 2-(hydroxy/alkoxyphenyl)pyridines VIIa/VIIb {cf. for example Organikum, VEB-Verlag, Berlin 1986, p.304–307}:

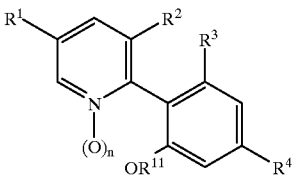

VIIa

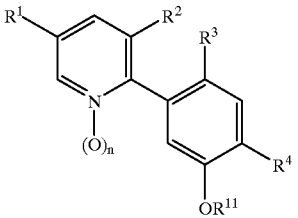

VIIb $R^{11}$ is hydrogen or $C_1$–$C_4$-alkyl such as methyl, ethyl and tert-butyl.

C) Reaction of a 2-(diaminophenyl)pyridine of the formula VIII with a carboxylic acid derivative or carbonic acid derivative {cf. also J. Backes, B. Heinz, W. G. Ried in Houben-Weyl, Methoden der Organischen Chemie, Georg Thieme Verlag Stuttgart, Vol. E8c 1994, p.216–376}:

VIIIa

→

I {X = —N($R^6$)—C(Z$R^5$)=N—
whose unsubstituted imino-
nitrogen is attached to b}

VIIIb

→

I {X = —N($R^6$)—C(Z$R^5$)=N—
whose unsubstituted imino-
nitrogen is attached to α}

With a view to the carboxylic acid derivatives/carbonic acid derivatives, solvents, reaction temperature, relative proportions and the preparation of the starting materials from the corresponding nitro derivatives, the specifications for method B) apply.

D) Diazotization of substituted 2-(benzaryl)pyridines of the formula I where Z$R^5$ is amino, and subsequent conversion of the diazonium salt into compounds I where
—Z$R^5$=cyano or halogen {for the Sandmeyer reaction, cf. for example Houben-Weyl, Methoden der Organischen Chemie, Georg Thieme Verlag Stuttgart, Vol. 5/4, 4th edition 1960, p.438ff.}, —Z—=sulfur {cf. for example Houben-Weyl, Methoden der Organischen Chemie, Georg Thieme Verlag Stuttgart, Vol. E11, 1984, p. 43 and 176}, —ZR$^5$=for example —CH$_2$—CH(Cl)—R$^8$, —CH$_2$—CH(Br)—R$^8$, —CH=CH—R$^8$, —CH=C(Cl)—R$^8$, —CH=C(Br)—R$^8$ {in general, these are products of a Meerwein arylation; cf. for example C. S. Rondestredt, Org. React. 11, (1960), 189, and H. P. Doyle et al., J. Org. Chem. 42, (1977), 2431}:

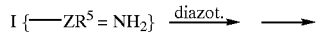
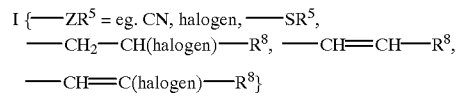

Generally, the diazonium salt is obtained in a conventional manner by reacting I where —ZR$^5$=amino in an aqueous acid solution, for example in hydrochloric acid, hydrobromic acid or sulfuric acid, with a nitrite such as sodium nitrite and potassium nitrite.

However, it is also possible to work under anhydrous conditions, for example in glacial acetic acid containing hydrogen chloride, in absolute alcohol, in a chlorinated hydrocarbon such as dichloromethane, chloroform, carbon tetrachloride and 1,2-dichloroethane, in a cyclic ether such as dioxane or tetrahydrofuran, in acetonitrile or in acetone, treating the starting material (I where —ZR$^5$=NH$_2$) with a nitrite such as tert-butyl nitrite and isopentyl nitrite.

The conversion of the resulting diazonium salt into the corresponding compound I where —ZR$^5$=cyano, chlorine, bromine or iodine is particularly preferably carried out by treatment with a solution or suspension of a copper(I)/copper(II) salt such as copper(I) cyanide, chloride, bromide and iodide, if desired in the presence of an alkali metal salt.

Compounds I where —Z—=sulfur are usually obtained by reacting the diazonium salt with a dialkyl disulfide such as dimethyl disulfide and diethyl disulfide, or with, for example, diallyl disulfide or dibenzyl disulfide.

The Meerwein arylation usually comprises the reaction of the diazonium salts with alkenes (here H$_2$C=CH—R$^8$) or alkynes (here HC≡C—R$^8$) in the presence of a catalytic to about equimolar amount of a copper(I)/copper(II) salt. Preference is given to using an excess of alkene or alkyne of up to 3000 mol %, based on the amount of the diazonium salt.

The reactions of the diazonium salt described above can be carried out, for example, in water, in aqueous hydrochloric acid or hydrobromic acid, in a ketone such as acetone, diethyl ketone and methyl ethyl ketone, in a nitrile such as acetonitrile, in an ether such as dioxane and tetrahydrofuran, in a chlorinated hydrocarbon such as dichloromethane or in an alcohol such as methanol and ethanol.

If not stated otherwise for the individual reactions, the reaction temperatures are usually between the melting point and the boiling point of the respective reaction mixture.

Preferably, all reaction partners are employed in about stoichiometric amounts, but an excess of one or the other component of up to 3000 mol % may also be advantageous.

E) Oxidation of compounds I where Z is sulfur:

Oxidation of a substituted 2-(benzaryl)pyridine I where Z is sulfur to I where Z=—SO— in a conventional manner {cf. for example Houben-Weyl, Methoden der Organischen Chemie, Georg Thieme Verlag Stuttgart, Vol. E 11/1, 1985, p. 702 ff., Vol. IX, 4th edition, 1955, p. 211}:

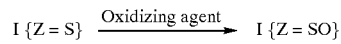

Suitable oxidizing agents are, for example, hydrogen peroxide, organic peroxides such as acetic peroxide, trifluoroacetic peroxide, m-chloroperbenzoic acid, tert-butyl hydroperoxide and tert-butyl hypochlorite, and inorganic compounds such as sodium metaiodate, chromic acid and nitric acid.

Depending on the oxidizing agent, the reaction is usually carried out in an organic acid such as acetic acid and trichloroacetic acid, in a chlorinated hydrocarbon such as methylene chloride, chloroform and 1,2-dichloroethane, in an aromatic hydrocarbon such as benzene, chlorobenzene and toluene or in a protic solvent such as methanol and ethanol. Mixtures of the solvents mentioned may also be suitable.

The reaction temperature is generally from (–30)° C. to the boiling point of the respective reaction mixture, the lower temperature range usually being preferred.

Starting material and oxidizing agent are advantageously employed in about stoichiometric amounts, but one or the other component may also be used in excess.

F) Oxidation of a substituted 2-(benzaryl)pyridine I, where Z is sulfur or —SO— to I where Z=—SO$_2$— in a conventional manner {cf. for example Houben-Weyl, Methoden der Organischen Chemie, Georg Thieme Verlag Stuttgart, Vol. E 11/2, 1985, p. 1132 ff and vol. IX, 4th edition, 1955, p. 222 ff.}:

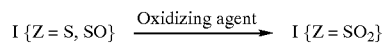

Suitable oxidizing agents are, for example, hydrogen peroxide, organic peroxides such as acetic peroxide, trifluoroacetic peroxide and m-chloroperbenzoic acid, furthermore inorganic oxidizing agents such as potassium permanganate. The presence of a catalyst, for example tungstate, may promote the course of the reaction.

In general, the reaction is carried out in an inert solvent, suitable solvents being, depending on the oxidizing agent, for example organic acids such as acetic acid and propionic acid, chlorinated hydrocarbons such as methylene chloride, chloroform and 1,2-dichloroethane, aromatic hydrocarbons or halogenated hydrocarbons such as benzene, chlorobenzene and toluene, or water. Mixtures of the solvents mentioned may also be suitable.

Usually, the reaction is carried out at from (–30)° C. to the boiling point of the respective reaction mixture, preferably at from 10° C. to the boiling point.

The starting material I where Z=sulfur or SO and the oxidizing agent are advantageously employed in about stoichiometric amounts. However, to optimize the conversion of the starting material, an excess of oxidizing agent may be advantageous G) Reaction of a substituted 2-(benzaryl)pyridine I where the group —ZR$^5$ is chlorine, bromine, alkylsulfonyl or haloalkylsulfonyl in a conventional manner with an alcohol, mercaptan or amine IX in the presence of a base:

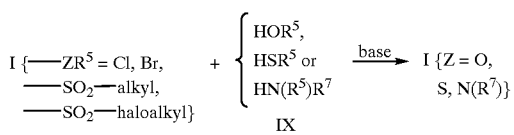

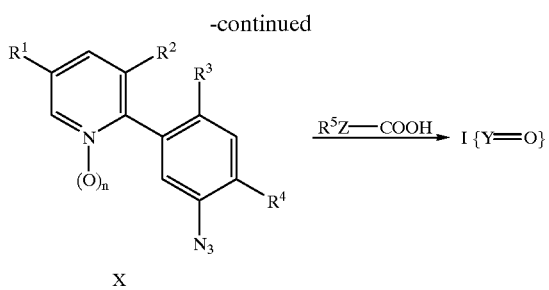

The reaction is advantageously carried out in an inert solvent, for example in an ether such as diethyl ether, methyl tert-butyl ether, dimethoxyethane, diethylene glycol dimethyl ether, tetrahydrofuran and dioxane, a ketone such as acetone, diethyl ketone, ethyl methyl ketone and cyclohexanone, a dipolar aprotic solvent such as acetonitrile, dimethylformamide, N-methylpyrrolidone and dimethyl sulfoxide, a protic solvent such as methanol and ethanol, an aromatic hydrocarbon which may be halogenated, if desired, such as benzene, chlorobenzene and 1,2-dichlorobenzene, a heteroaromatic solvent such as pyridine and quinoline or in a mixture of such solvents. Preference is given to tetrahydrofuran, acetone, diethyl ketone and dimethyl formamide.

Suitable bases are, for example, the hydroxides, hydrides, alkoxides, carbonates or bicarbonates of alkali metal and alkaline earth metal cations, tertiary aliphatic amines such as triethylamine, N-methylmorpholine and N-ethyl-N,N-diisopropyl-amine, bi- and tricyclic amines such as diazabicyclooctane (DABCO), amidine bases such as diazabicycloundecene (DBU), or aromatic nitrogen bases such as pyridine, 4-dimethylaminopyridine and quinoline. Combinations of different bases may also be suitable. Preferred bases are sodium hydride, sodium hydroxide, sodium carbonate, potassium carbonate, sodium methoxide, sodium ethoxide and potassium tert-butoxide.

The starting materials are usually employed in about stoichiometric amounts, but it may be advantageous to use an excess of one or the other component with regard to the practice of the process or in order to achieve a very complete conversion of the starting material I {—$ZR^5$=Cl, Br, —$SO_2$-alkyl, —$SO_2$-haloalkyl}.

The molar ratio of alcohol, mercaptan or amine IX to base is generally from 1:1 to 1:3.

The concentration of the starting materials in the solvent is usually from 0.1 to 5.0 mol/l.

The reaction can be carried out at from 0° C. to the reflux temperature of the respective reaction mixture.

H) Conversion of a 2-(aminophenyl)pyridine of the formula IIa into the corresponding azide X and subsequent reaction of X with a carboxylic acid $R^5Z$—COOH:

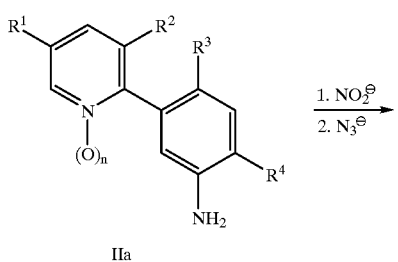

The conversion of IIa into X is generally carried out by treatment with an alkyl nitrite, preferably tert-butyl nitrite, and reaction of the resulting diazonium ion with an azide, preferably an alkali metal azide such as sodium azide (cf. for example K. Kanakarajan, K. Maider & A. W. Czarnik in Synthesis 1988, p. 566).

With respect to the subsequent reaction of X with $R^5Z$—COOH, reference may be made to R. Garner, E. B. Mullock & H. Suschitzky, J. Chem. Soc. 1966, p. 1980. For the formation of the oxazole ring, it may be advantageous to carry out the reaction in the presence of phosphoric acid or polyphosphoric acid.

Unless stated otherwise, all the processes described above are advantageously carried out under atmospheric pressure or under the autogenous pressure of the reaction mixture in question.

The work-up of the reaction mixtures is usually carried out in a conventional manner. Unless stated otherwise in the processes described above, the products of value are obtained, for example, after the dilution of the reaction solution with water by filtration, crystallization or solvent extraction, or by removing the solvent, partitioning the residue in a mixture of water and a suitable organic solvent and working up the organic phase to afford the product.

In general, the substituted 2-(benzaryl)pyridines I are preparable by one of the abovementioned synthetic methods. However, for economic reasons or reasons of process efficiency, it may be advantageous to prepare some of the compounds I from (similar 2-(benzaryl)pyridines but which differ in particular in the meaning of the radical $ZR^5$ in a conventional manner, for example by ester hydrolysis, esterification, amidation, acetalization, acetal hydrolysis, condensation reaction, Wittig reaction, Peterson olefination, etherification, alkylation, oxidation or reduction.

The substituted 2-(benzaryl)pyridines I can be obtained as isomer mixtures in the preparation; however, if desired, these can be separated into largely pure isomers using customary methods such as crystallization or chromatography, including chromatography over an optically active adsorbent. Pure optically active isomers can be prepared advantageously from appropriate optically active starting materials.

Agriculturally useful salts of the compounds I can be formed by reaction with a base of the corresponding cation, preferably an alkali metal hydroxide or hydride, or by reaction with an acid of the corresponding anion, preferably of hydrochloric acid, hydrobromic acid, sulfuric acid, phosphoric acid or nitric acid.

Salts of I where the metal ion is not an alkali metal ion can be prepared by cation exchange of the corresponding alkali metal salt in a conventional manner, similarly ammonium, phosphonium, sulfonium and sulfoxonium salts by means of ammonia, phosphonium, sulfonium or sulfoxonium hydroxides.

The compounds I and their agriculturally useful salts are suitable, both in the form of isomer mixtures and in the form of the pure isomers, for use as herbicides. The herbicidal compositions comprising I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Taking into account the diversity of application methods, the compounds I, or herbicidal compositions comprising them, can additionally be employed in a further number of crop plants for eliminating undesirable plants. Examples of suitable crops are the following: *Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N.rustica*), *Olea europaea, Oryza sativa , Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

In addition, the compounds I may also be used in crops which tolerate the action of herbicides owing to breeding, including genetic engineering methods.

Moreover, the substituted 2-(benzaryl)pyridines I are also suitable for the desiccation and/or defoliation of plants.

As desiccants, they are suitable, in particular, for desiccating the aerial parts of crop plants such as potatoes, oilseed rape, sunflowers and soybeans. This allows completely mechanical harvesting of these important crop plants.

Also of economic interest is the facilitation of harvesting, which is made possible by dehiscence, or reduction of the adherence to the tree, both concentrated over a period of time, in citrus fruit, olives or other species and varieties of pomaceous fruit, stone fruit and nuts. The same mechanism, ie. the promotion of the formation of abscission tissue between fruit or leaf and shoot of the plants, is also important for readily controllable defoliation of useful plants, in particular cotton.

Moreover, shortening the period within which the individual cotton plants mature results in improved fiber quality after harvesting.

The compounds I, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for scattering, or granules, by means of spraying, atomizing, dusting, scattering or watering. The use forms depend on the intended applications; in any case, they should ensure a very fine distribution of the active compounds according to the invention.

Suitable inert auxiliaries are essentially: mineral oil fractions of medium to high boiling point, such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and 2 formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for scattering and dusts can be prepared by mixing or grinding the active compounds together with a solid carrier.

Granules, eg. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise approximately from 0.001 to 98% by weight, preferably 0.01 to 95% by weight of at least one active compound. The active compounds I are employed in a purity of from 90% to 100%, preferably 95% to 100% (according to the NMR spectrum).

The formulation examples which follow illustrate the preparation of such preparations:

I. 20 parts by weight of the compound No. Ic.001 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound No. Ic.041 are dissolved in a mixture composed of 40 parts by weight of cyclohexanone, 30 parts by weight of isobutanol, 20 parts by weight of the adduct of 7 mol of ethylene oxide to 1 mol of isooctyl-phenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the active compound No. Ic.042 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of the active compound No. Ic.100 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the active compound No. Ic.138 are mixed with 97 parts by weight of finely divided kaolin. This gives a dust which comprises 3% by weight of the active compound.

VI. 20 parts by weight of the active compound No. Ic.139 are mixed intimately with 2 parts by weight of calcium dodecyl-benzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. Ic.176 is dissolved in a mixture composed of 70 parts by weight of cyclohexanone, 20 parts by weight of ethoxylated isooctylphenol and 10 parts by weight of ethoxylated castor oil. The mixture can then be diluted with water to the desired concentration of active compound. This gives a stable emulsion concentrate.

VIII. 1 part by weight of the compound No. Ic.233 is dissolved in a mixture composed of 80 parts by weight of cyclohexane and 20 parts by weight of Wettol® EM 31 (=nonionic emulsifier based on ethoxylated castor oil; BASF AG). The mixture can then be diluted with water to the desired concentration of active compound. This gives a stable emulsion concentrate.

The active compounds I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active compounds reach the leaves of undesirable plants growing underneath, or the bare soil surface (post-directed, lay-by).

The rates of application of active compound I are from 0.001 to 3.0, preferably 0.01 to 1.0, kg/ha of active substance (a.s.), depending on the control target, the season, the target plants and the growth stage.

To widen the spectrum of action and to achieve synergistic effects, the substituted 2-(benzaryl)pyridines I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, aryloxy/hetaryloxyalkanoic acids and their derivatives, benzoic acid and its derivatives, benzothiadiazinones, 2-(hetaroyl/aroyl)-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetra-hydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or else concomitantly in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

PREPARATION EXAMPLES

Example 1

2-(2-Amino-4-chloro-6-fluorobenzothiazol-7-yl)-3-chloro-5-trifluoromethylpyridine (Compound No. Ic.081)

At about 20° C., a solution of 37 g (234 mmol) of bromine in 10 ml of glacial acetic acid was added over a period of 10 minutes to a solution of 38 g (117 mmol) of 2-(3-amino-4-chloro-6-fluorophenyl)-3-chloro-5-trifluoromethylpyridine and 38 g (468 mmol) of sodium thiocyanate in 500 ml of glacial acetic acid. The reaction mixture was subsequently stirred at room temperature for 10 hours and then poured into 2 l of water. The product was then extracted with 3×500 ml of ethyl acetate. The combined organic phases were dried over magnesium sulfate and (finally concentrated. The crude product was purified by silica gel chromatography (eluent: cyclohexane/ethyl acetate =4:1→1:1). Yield: 13%; m.p.: 230–235° C.

Example 2

Compound No. Ic.309

A mixture of 3.8 g (10.0 mmol) of Ic.081, 100 ml of acetic anhydride and about 20 mg of 4-N,N-dimethylaminopyridine (DMAP) was stirred at room temperature for 20 hours. The reaction mixture was subsequently poured into 500 ml of water. The product was extracted from the aqueous phase using 2×250 ml of ethyl acetate. The organic phase was dried over magnesium sulfate and concentrated. The crude product was purified by silica gel chromatography (eluent: cyclohexane/ethyl acetate=4:1) and then recrystallized from cyclohexane/ethyl acetate (9:1). Yield: 300 mg; m.p.: 220–222° C.

Example 3

Compound No. Ic.041

At 80–90° C., 1.0 g (2.6 mmol) of Ic.081 was dissolved in 60 ml of concentrated hydrochloric acid over a period of 1 hour. The starting material was then diazotized at 0–5° C. using 0.2 g (2.9 mmol) of sodium nitrite in 10 ml of water. The resulting reaction mixture was added dropwise to a solution of 0.2 g (2.9 mmol) of copper(I) chloride and 2.0 g (34 mmol) of sodium chloride in 50 ml of concentrated hydrochloric acid. The mixture was then refluxed for 1 hour. The mixture was allowed to cool and the product that had formed was extracted with 3×50 ml of methylene chloride. The combined organic phases were dried and finally concentrated. The crude product was purified by silica gel chromatography (eluent: cyclohexane/ethyl acetate=4:1). Yield: 29%; m.p.: 131° C.

Example 4

Compound No. Ic.042

A suspension of 4.5 g (20 mmol) of copper(II) bromide in 50 ml of acetonitrile was added to a mixture of 7.6 g (20 mmol) of Ic.081, 2.6 g (25 mmol) of tert-butyl nitrite and 50 ml of acetonitrile. The reaction mixture was subsequently stirred at about 20° C. for 4 hours and then added to 1.5 l of 20% strength by weight hydrochloric acid with stirring. The resulting product of value was then extracted with 2×300 ml of ethyl acetate. The organic phase was washed with 100 ml of saturated aqueous sodium chloride solution, dried over magnesium sulfate and finally concentrated. The crude product was purified by silica gel chromatography (eluent: cyclohexane/ethyl acetate=4:1). Yield: 15%; m.p.: 135–143° C.

Example 5

Compound No. Ic.100

At about 20° C., 5 ml of tert-butyl nitrite were added to 1.0 g (2.6 mmol) of Ic.081 in a mixture of 50 ml of dichloromethane and 5 ml of tetrahydrofuran. The mixture was subsequently stirred for 5 minutes and then mixed with 5 ml (53 mmol) of dimethyl disulfide. The mixture was then stirred for a further 10 hours and concentrated. The crude product was purified by silica gel chromatography (eluent: cyclohexane/ethyl acetate=4:1). Yield: 28%; m.p.: 100–103° C.

Example 6

Compound No. Ic.043

At about 20° C., 0.4 g of a 30% strength by weight solution of sodium methoxide in methanol (= 2.0 mmol of sodium methoxide) was added to 0.4 g (0.9 mmol) of Ic.081 in 20 ml of methanol. The mixture was stirred for 13 hours and then concentrated. The crude product was purified by silica gel chromatography (eluent: cyclohexane/ethyl acetate=4:1). Yield: 36%; m.p.: 100–103° C.

Example 7

Compound No. Ic.001

At (−78)° C., 0.7 ml of a 1.6 M solution of n-butyllithium in cyclohexane (= 1.1 mol of n-butyllithium) was added to 0.4 g (0.9 mmol) of 2-(2-bromo-4-chloro-6-fluorobenzothiazol-7-yl)-3-chloro-5-trifluoromethylpyridine in 30 ml of tetrahydrofuran. The mixture was subsequently stirred at (−78)° C. for 1 hour, after which cooling was removed. The mixture was stirred at about 20° C. for a further 30 minutes and the reaction was finally ended by the addition of 30 ml of methyl tert-butyl ether und 20 ml of saturated aqueous ammonium chloride solution. The organic phase was separated off, dried over magnesium sulfate and then concentrated. The crude product was purified by silica gel chromatography (eluent: cyclohexane/ethyl acetate=4:1). Yield: 9%; m.p.: 79–85° C.

Example 8

Compound No. Ic.138

At 0° C., 0.8 g of m-chloroperbenzoic acid (50–55% strength; 2.4 mmol) was added a little at a time to a mixture of 1.0 g (2.4 mmol) of Ic.100, 0.5 g (6.0 mmol) of sodium bicarbonate and 8 ml of dichloromethane. The mixture was then stirred at 0° C. for 3 hours, after which the resulting suspension was stirred into a mixture of 100 ml of saturated aqueous sodium bicarbonate (solution and 20 ml of saturated aqueous sodium thiosulfate solution ($Na_2S_2O_3$). The resulting product of value was subsequently extracted from the aqueous phase using 100 ml of dichloromethane. The combined organic extracts were dried over magnesium sulfate and then concentrated. The crude product was purified by silica gel chromatography (eluent: cyclohexane/ethyl acetate=4:1). Yield: 39%; m.p.: 130–132° C.

Example 9

Compound No. Ic.176

At 0° C., 3.2 g of m-chloroperbenzoic acid (50–55% strength; 9.6 mmol) were added a little at a time to a mixture of 0.9 g (2.2 mmol) of Ic.100, 1.0 g (12.0 mmol) of sodium bicarbonate and 80 ml of dichloromethane. The mixture was then stirred at about 20° C. for 15 hours, after which the resulting suspension was stirred into a mixture of 150 ml of saturated aqueous sodium bicarbonate solution and 30 ml of saturated aqueous sodium thiosulfate solution ($Na_2S_2O_3$). The resulting product of value was subsequently extracted from the aqueous phase using 150 ml of dichloromethane. The combined organic extracts were dried over magnesium sulfate and then concentrated. The crude product was purified by recrystallization from cyclohexane/ethyl acetate (9:1). Yield: 41%; m.p.: 164–165° C.

Example 10

Compound No. Ic.016

0.5 g (3.5 mmol) of 2-chloro-1,1,1-trimethoxyethane was added to 0.8 g (2.3 mmol) of 2-(2-amino-4-chloro-6-fluoro-3-hydroxyphenyl)-3-chloro-5-trifluoromethylpyridine in 15 ml of ethanol. The mixture was subsequently refluxed for 16 hours, after which the reaction mixture was concentrated. The crude product was purified by silica gel chromatography (eluent: cyclohexane/ethyl acetate =9:1). Yield: 54%.

Intermediate 10.1

2-(4-Chloro-6-fluoro-3-hydroxy-2-nitrophenyl)-3-chloro-5-trifluoromethylpyridine 0.24 ml (5.8 mmol) of 100% strength nitric acid was added to 1.9 g (5.8 mmol) of 2-(4-chloro-2-fluoro-5-hydroxyphenyl)-3-chloro-5-trifluoromethylpyridine in 50 ml of concentrated sulfuric acid. The reaction mixture was stirred at about 20° C. for 10 hours and then poured into 100 ml of ice-water. The solids were subsequently removed and dried at 40° C. in a vacuum drying cabinet. Yield: 79%; m.p.: 67–72° C.

Intermediate 10.2

2-(2-Amino-4-chloro-6-fluoro-3-hydroxyphenyl)-3-chloro-5-trifluoromethylpyridine 770 mg (13.7 mmol) of iron powder were added to 1.7 g (4.6 mmol) of 2-(4-chloro-2-fluoro-5-hydroxy-6- nitrophenyl)-3-chloro-5-trifluoromethylpyridine in 9 ml of glacial acetic acid and 18 ml of methanol. The reaction mixture was refluxed for 15 hours with stirring and then concentrated under reduced pressure. The residue was taken up in 100 ml of ethyl acetate. Undissolved components were then filtered off. The filtrate was washed with 20 ml of water, dried over magnesium sulfate and finally concentrated. Yield: 96%; oil.

Example 11

Compound No. Ir.003

A solution of 5 g (14 mmol) of 2-chloro-5-(3-chloro-5-trifluoro-methyl-2-pyridyl)-4-fluorophenyl azide in 25 ml of propionic acid was refluxed for 4 hours. The reaction mixture was subsequently mixed with 100 ml of water and 30 ml of methyl tert-butyl ether. The aqueous phase was then separated off and the resulting product of value was extracted two times with 30 ml of methyl tert-butyl ether each time. The combined organic phases were washed with saturated aqueous sodium bicarbonate solution, dried over magnesium sulfate and finally concentrated. The crude product was purified by silica gel chromatography (eluent: cyclohexane/ethyl acetate=9:1). Yield: 43%;

$^1$H NMR (270 MHz; in CDCl$_3$): δ [ppm]=1.42 (t, 3H), 2.96 (q, 2H), 7.29 (d, 1H), 8.15 (s, 1H), 8.94 (s, 1H).

Intermediate 11.1

2-Chloro-5-(3-chloro-5-trifluoromethyl-2-pyridyl)-4-fluorophenyl azide

With ice-cooling, initially 9.5 g (92 mmol) of tert-butyl nitrite were added dropwise to a solution of 20 g (62 mmol) of 2-chloro-5-(3-chloro-5-trifluoromethyl-2-pyridyl)-4-fluoroaniline in 40 ml of trifluoroacetic acid, and—with strong evolution of gas—6 g (92 mmol) of sodium azide were then added a little at a time. The mixture was stirred for 16 hours, and a further 15 ml of trifluoroacetic acid and 1.7 g (17 mmol) of tert-butyl nitrite were then added to the reaction mixture. Stirring was subsequently continued for another 30 minutes, and the mixture was then poured onto 0.3 l of ice-water. The resulting solid fraction was separated off and washed with 50 ml of water. For purification, the crude product was initially dissolved in 100 ml of toluene. The resulting toluene phase was then washed with saturated aqueous sodium bicarbonate solution, dried over magnesium sulfate and finally concentrated. Yield: 90%;

$^1$H NMR (270 MHz; in CDCl$_3$): δ [ppm]=7.29 (m, 2H), 8.09 (d, 1H), 8.88 (d, 1H).

Use Examples (Herbicidal Activity)

The herbicidal activity of the substituted 2-(benzaryl) pyridines I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active compounds, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this was adversely affected by the active compounds.

For the post-emergence treatment, the test plants were first grown to a height of 3 to 15 cm, depending on the plant habit, and only then treated with the active compounds which had been suspended or emulsified in water. For this purpose, the test plants were either sown directly and grown in the same containers, or they were first grown separately as seedlings and transplanted into the test containers a few days prior to treatment. The rate of application for the post-emergence treatment was 7.8 or 3.9 g/ha of a.s. (active substance).

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments belonged to the following species:

| Scientific name | Common Name |
| --- | --- |
| Amaranthus retroflexus | redroot pigweed |
| Galium aparine | catchweed bedstraw |
| Ipomoea species | morningglory |
| Solanum nigrum | black nightshade |
| Oryza sativa | rice |

The compound No. Ic.041, applied post-emergence, showed very good and selective herbicidal activity against Amaranthus retroflexus, Galium aparine, Ipomoea species and Solanum nigrum in rice crops at rates of application of 7.8 and 3.9 g/ha of a.s.

Use Examples (Desiccant/defoliant Activity)

The test plants used were young cotton plants with 4 leaves (without cotyledons) which had been grown under greenhouse conditions (relative atmospheric humidity 50 to 70%; day/night temperature 27/20° C.).

The young cotton plants were subjected to foliar treatment to runoff point with aqueous preparations of the active compounds I (with an addition of 0.15% by weight of the fatty alcohol alkoxide Plurafac® LF 700$^1$), based on the spray mixture). The amount of water applied was 1000 l/ha (converted). After 13 days, the number of leaves shed and the degree of defoliation in % were determined.

$^1$) a low-foam, nonionic surfactant from BASF AG

No leaves were shed in the untreated control plants.

We claim:

1. A 2-(benzaryl)pyridine of formula I

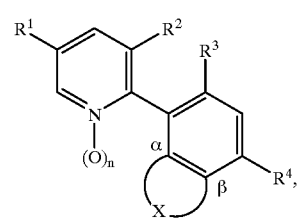

wherein n is zero or 1;

R$^1$ is hydrogen, cyano, nitro, amino, hydroxyl, mercapto, hydroxysulfonyl, chlorosulfonyl, aminosulfonyl, halogen, C$_1$–C$_6$-alkyl, C$_1$–C$_6$-haloalkyl, C$_1$–C$_6$-alkoxy, C$_1$–C$_6$-haloalkoxy, C$_1$–C$_6$-alkylthio, C$_1$–C$_6$- haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, $C_1$–$C_6$-alkylaminosulfonyl or di($C_1$–$C_6$-alkyl)aminosulfonyl;

$R^2$ and $R^3$ independently of one another are each hydrogen or halogen;

$R^4$ is cyano, hydroxyl, halogen, $C_1$–$C_6$-alkoxy or benzyloxy, wherein the phenyl ring is unsubstituted or carries one to three substituents, in each case selected from the group consisting of hydroxyl, halogen, $C_1$–$C_6$-alkyl, $C_1$–$C_6$-haloalkyl, $C_1$–$C_6$-alkoxy, $C_1$–$C_6$-haloalkoxy, hydroxycarbonyl, ($C_1$–$C_6$-alkoxy)carbonyl and ($C_1$–$C_6$-alkoxy)carbonyl-$C_1$–$C_6$-alkoxy;

X is the —Y—C(ZR$^5$)=N— moiety of a hetaryl ring, wherein the nitrogen is attached to the carbon marked β and Y is oxygen or sulfur;

Z is a chemical bond, oxygen, sulfur, —S(O)—, —SO$_2$— or —N(R$^7$)—;

$R^5$ and $R^7$ independently of one another are each hydrogen, $C_1$–$C_6$-alkyl, $C_1$–$C_6$-haloalkyl, cyano-$C_1$–$C_4$-alkyl, hydroxy-$C_1$–$C_4$-alkyl, $C_3$–$C_6$-alkenyl, cyano-$C_3$–$C_6$-alkenyl, $C_3$–$C_6$-haloalkenyl, $C_3$–$C_6$-alkynyl, cyano-$C_3$–$C_6$-alkynyl, $C_3$–$C_6$-haloalkynyl, $C_1$–$C_4$-alkoxy-$C_1$–$C_4$-alkyl, $C_1$–$C_4$-haloalkoxy-$C_1$–$C_4$-alkyl, $C_3$–$C_4$-alkenyloxy-$C_1$–$C_4$-alkyl, $C_3$–$C_4$-alkynyloxy-$C_1$–$C_4$-alkyl, $C_3$–$C_8$-cycloalkyloxy-$C_1$–$C_4$-alkyl, amino-$C_1$–$C_4$-alkyl, $C_1$–$C_4$-alkylamino-$C_1$–$C_4$-alkyl, di($C_1$–$C_4$-alkyl)amino-$C_1$–$C_4$-alkyl, $C_1$–$C_4$-alkylthio-$C_1$–$C_4$-alkyl, $C_1$–$C_4$-haloalkylthio-$C_1$–$C_4$-alkyl, $C_3$–$C_4$-alkenylthio-$C_1$–$C_4$-alkyl, $C_3$–$C_4$-alkynylthio-$C_1$–$C_4$-alkyl, $C_1$–$C_4$-alkylsulfinyl-$C_1$–$C_4$-alkyl, $C_1$–$C_4$-haloalkylsulfinyl-$C_1$–$C_4$-alkyl, $C_3$–$C_4$-alkenylsulfinyl-$C_1$–$C_4$-alkyl, $C_3$–$C_4$-alkynylsulfinyl-$C_1$–$C_4$-alkyl, $C_1$–$C_4$-alkylsulfonyl-$C_1$–$C_4$-alkyl, $C_1$–$C_4$-haloalkylsulfonyl-$C_1$–$C_4$-alkyl, $C_3$–$C_4$-alkenylsulfonyl-$C_1$–$C_4$-alkyl, $C_3$–$C_4$-alkynylsulfonyl-$C_1$–$C_4$-alkyl, hydroxycarbonyl-$C_1$–$C_4$-alkyl, ($C_1$–$C_4$-alkoxy)carbonyl-$C_1$–$C_4$-alkyl, ($C_1$–$C_4$-alkylthio)carbonyl-$C_1$–$C_4$-alkyl, aminocarbonyl-$C_1$–$C_4$-alkyl, $C_1$–$C_4$-alkylaminocarbonyl-$C_1$–$C_4$-alkyl, di($C_1$–$C_4$-alkyl)aminocarbonyl-$C_1$–$C_4$-alkyl, $C_3$–$C_8$-cycloalkyl, $C_3$–$C_8$-cycloalkyl-$C_1$–$C_4$-alkyl, phenyl or phenyl-$C_1$–$C_4$-alkyl, wherein a methylene ring member of the cycloalkyl ring optionally carries an =O or =S substituent to form a carbonyl or thiocarbonyl ring member, and wherein each cycloalkyl and phenyl ring is unsubstituted or carries one to four substituents, in each case selected from the group consisting of cyano, nitro, amino, hydroxyl, carboxy, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkoxy)carbonyl, ($C_1$–$C_4$-alkyl)carbonyl, ($C_1$–$C_4$-haloalkyl)carbonyl, ($C_1$–$C_4$-alkyl)carbonyloxy, ($C_1$–$C_4$-haloalkyl)carbonyloxy and di($C_1$–$C_4$-alkyl)amino, or, if Z is a chemical bond, $R^5$ is also hydrogen, cyano, mercapto, amino, halogen, —CH$_2$—CH(halogen)—R$^8$, —CH=CH—R$^8$ or —CH=C(halogen)-R$^8$, wherein $R^8$ is hydroxycarbonyl, ($C_1$–$C_4$-alkoxy)carbonyl, ($C_1$–$C_4$-alkylthio)carbonyl, aminocarbonyl, $C_1$–$C_4$-alkylaminocarbonyl or di($C_1$–$C_4$-alkyl)aminocarbonyl, or an agriculturally useful salt of the compound I.

2. The 2-(benzaryl)pyridine of formula I defined in claim 1 or its salt wherein $R^1$ is $C_1$–$C_4$-haloalkyl or $C_1$–$C_4$-alkylsulfonyl.

3. The 2-(benzaryl)pyridine of formula I defined in claim 1 or its salt wherein $R^4$ is cyano or halogen.

4. The 2-(benzaryl)pyridine of formula I defined in claim 1, or its salt wherein $R^2$ is halogen.

5. The 2-(benzaryl)pyridine of formula I defined in claim 1, or its salt wherein $R^3$ is hydrogen, fluorine or chlorine.

6. The 2-(benzaryl)pyridine of formula I defined in claim 1, or its salt wherein the carbocyclic radical represented by $R^5$ or $R^7$ is unsubstituted or carries one of said substituents.

7. A composition comprising a herbicidally effective amount of at least one 2-(benzaryl)pyridine of formula I or the agriculturally useful salt of I defined in claim 1 and at least one inert liquid or solid carrier and optionally at least one surfactant.

8. A composition for the desiccation or defoliation of plants, comprising an amount of at least one 2-(benzaryl)pyridine of formula I or the agriculturally useful salt of I defined in claim 1, which acts as a desiccant or defoliant, and at least one inert liquid or solid carrier and optionally at least one surfactant.

9. A method for controlling undesirable vegetation, which comprises allowing a herbicidally effective amount of at least one 2-(benzaryl)pyridine of formula I or the agriculturally useful salt of I defined in claim 1, to act on plants, their habitat or on seeds.

10. A method for the desiccation or defoliation of plants, which comprises allowing an amount of at least one 2-(benzaryl)pyridine of formula I or the agriculturally useful salt of I defined in claim 1, which acts as a desiccant or defoliant, to act on plants.

11. The method defined in claim 10, wherein the plants are cotton plants.

12. A process for preparing substituted 2-(benzaryl)pyridines of the formula I as claimed in claim 1 where Z is sulfur, which comprises diazotizing a substituted 2-(benzaryl)pyridine I, where ZR$^5$ is amino, and subsequently reacting the resulting diazonium salt with a dialkyl disulfide of the formula R$^5$S—SR$^5$.

13. A process for preparing substituted 2-(benzaryl)pyridines of the formula I as claimed in claim 1 where ZR$^5$ is —CH$_2$—CH(Cl)—R$^8$, —CH$_2$—CH(Br)—R$^8$, —CH=CH—R$^8$, —CH=C(Cl)—R$^8$ or —CH=C(Br)—R$^8$, which comprises diazotizing a substituted 2-(benzaryl)pyridine I where ZR$^5$ is amino, and subsequently reacting the resulting diazonium salt with an alkene of the formula H$_2$C=CH—R$^8$ or an alkyne of the formula HC≡C—R$^8$ in the presence of a copper(I)/copper(II) salt.

14. A process for preparing substituted 2-(benzaryl)pyridines of the formula I as claimed in claim 1 where Z is —S(O)— or —SO$_2$—, which comprises oxidizing a substituted 2-(benzaryl)pyridine I where Z is sulfur.

* * * * *